(12) United States Patent
Cozzone et al.

(10) Patent No.: US 6,524,785 B1
(45) Date of Patent: Feb. 25, 2003

(54) PERFUSION AND/OR PRESERVATION AND/OR RE-PERFUSION SOLUTION DURING ORGAN TRANSPLANT

(75) Inventors: Patrick Cozzone, Marseille (FR); Monique Bernard, Marseille (FR)

(73) Assignee: Centre National de la Recherche Scientifique, Paris Cedex (FR)

( * ) Notice: Subject to any disclaimer, the term of this patent is extended or adjusted under 35 U.S.C. 154(b) by 0 days.

(21) Appl. No.: 09/582,996

(22) PCT Filed: Nov. 5, 1999

(86) PCT No.: PCT/FR99/02711

§ 371 (c)(1),
(2), (4) Date: Aug. 25, 2000

(87) PCT Pub. No.: WO00/27189

PCT Pub. Date: May 18, 2000

(30) Foreign Application Priority Data

Nov. 10, 1998 (FR) ............................................. 98 14132

(51) Int. Cl.[7] ................................................. A01N 1/02
(52) U.S. Cl. ........................... 435/1.1; 435/1.2; 514/46; 514/47; 562/560; 562/563; 536/26.1
(58) Field of Search ..................... 514/46, 47; 435/1.1, 435/1.2; 562/560, 563; 536/26.1

(56) References Cited

U.S. PATENT DOCUMENTS 4,920,044 A * 4/1990 Bretan, Jr. ..................... 435/1
5,290,766 A   3/1994 Choong .......................... 514/3
5,407,793 A   4/1995 Del Nido et al. ................ 435/1

FOREIGN PATENT DOCUMENTS

FR          2 695 827          3/1994

OTHER PUBLICATIONS

Kevelaitis et al. Poststorage Diastolic Abnormalities of Heart Transplant: Is Vascular Dysfunction or Myocardial Contracture the Culprit, The Journal of Heart and Lung Transplantation, vol. 15, No. 5, pp. 461–469. May 1996.*

By E. Kevelaitis et al., "Poststorage Diastolic Abnormalities of Heart Transplants: Is Vascular Dysfunction or Myocardial Contracture the Culprit?", *The Journal of Heart and Lung Transplantation*, vol. 15, No. 5, 1996, pp. 461–469.

* cited by examiner

*Primary Examiner*—Christopher S. F. Low
*Assistant Examiner*—Anish Gupta
(74) *Attorney, Agent, or Firm*—Young & Thompson

(57) ABSTRACT

The invention concerns a perfusion and/or preservation and/or re-perfusion solution during organ transplant, in particular the cardiac organ, containing the following elements: $K^+$ in the range of about 4 to about 7 mM; $Ca^{2+}$ in the range of about 0.2 to about 0.3 mM; $Mg^{2+}$ in the range of about 13 to about 16 mM; glutamate in the range of about 18 to about 22 mM; arginine in the range of about 2 to about 4 mM; adenosine in the range of about 0.5 to 1 mM.

12 Claims, 21 Drawing Sheets

EXPERIMENTAL PROTOCOL 1

EXPERIMENTAL PROTOCOL 2

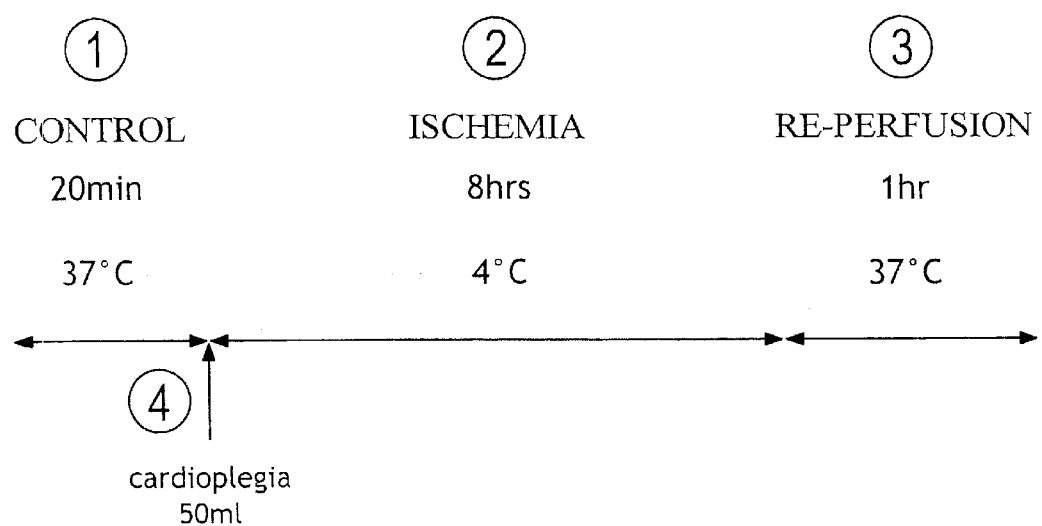

Recovery of the hemodynamic parameters during re-perfusion

EXPERIMENTAL PROTOCOL 4

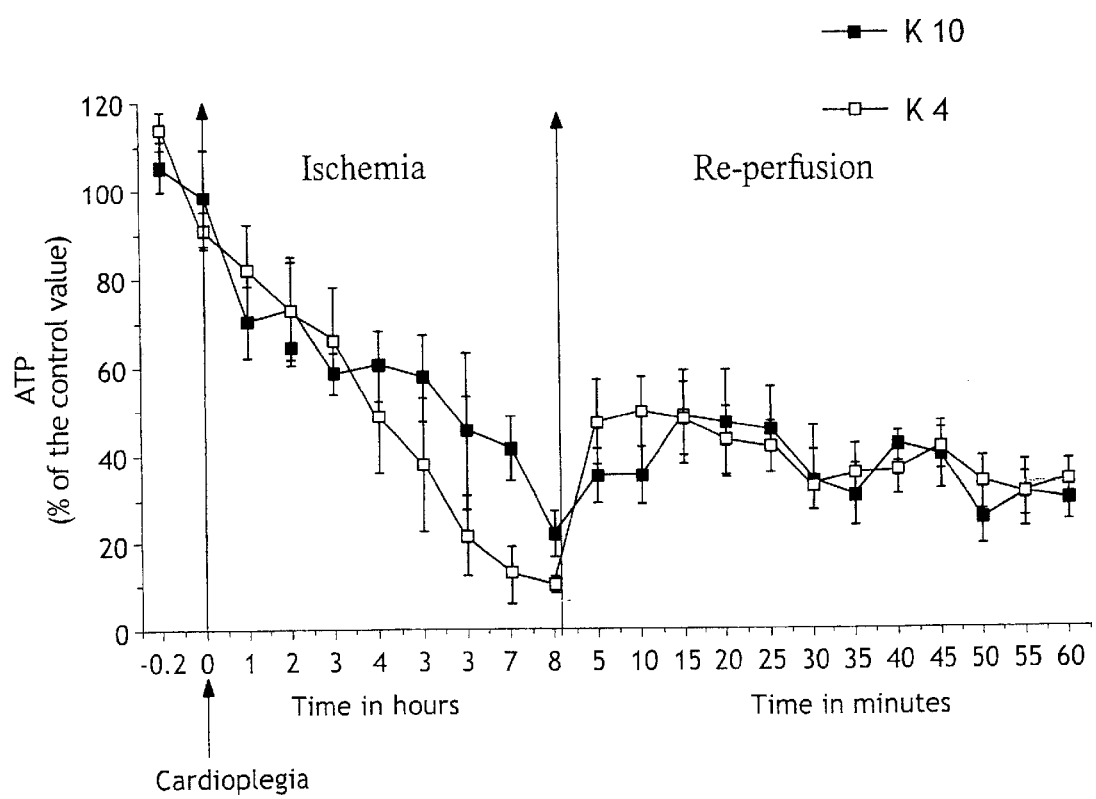

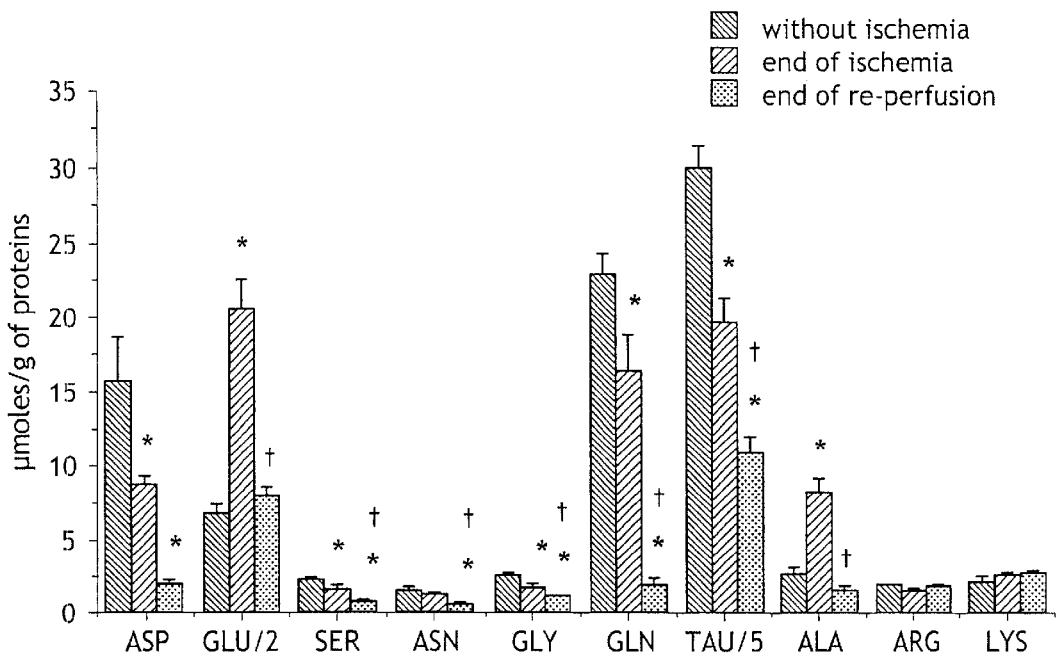
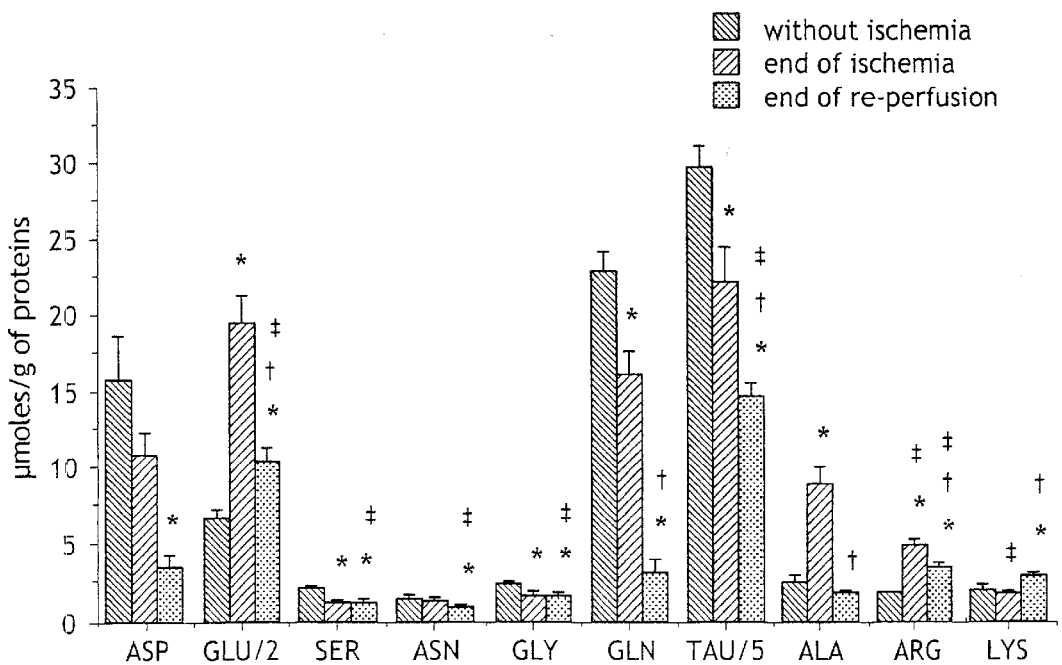

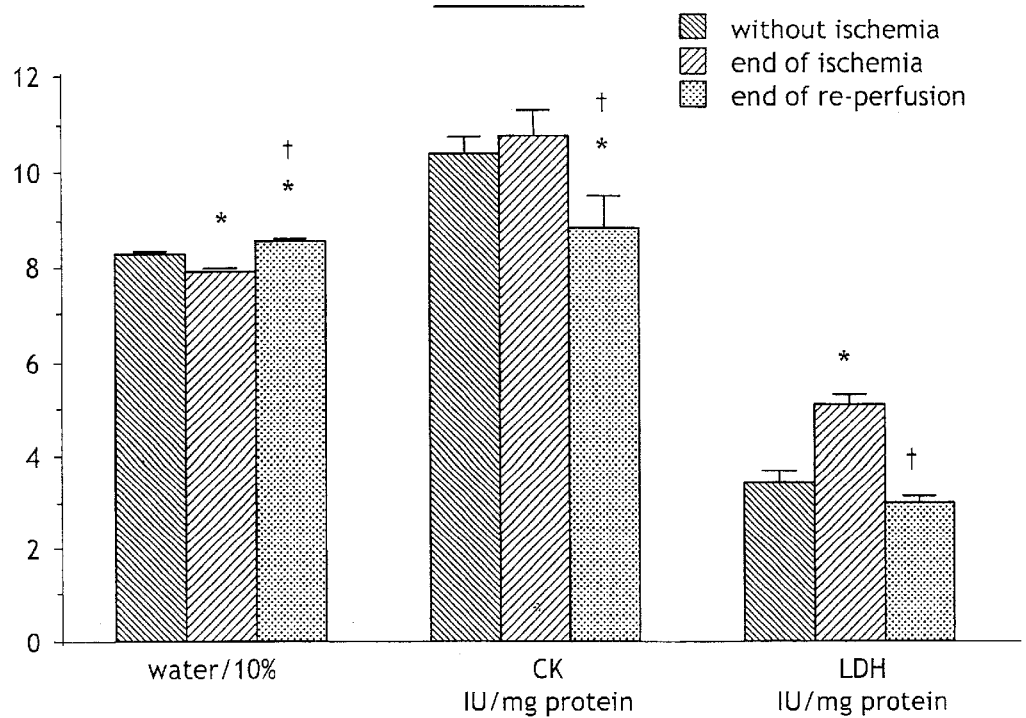
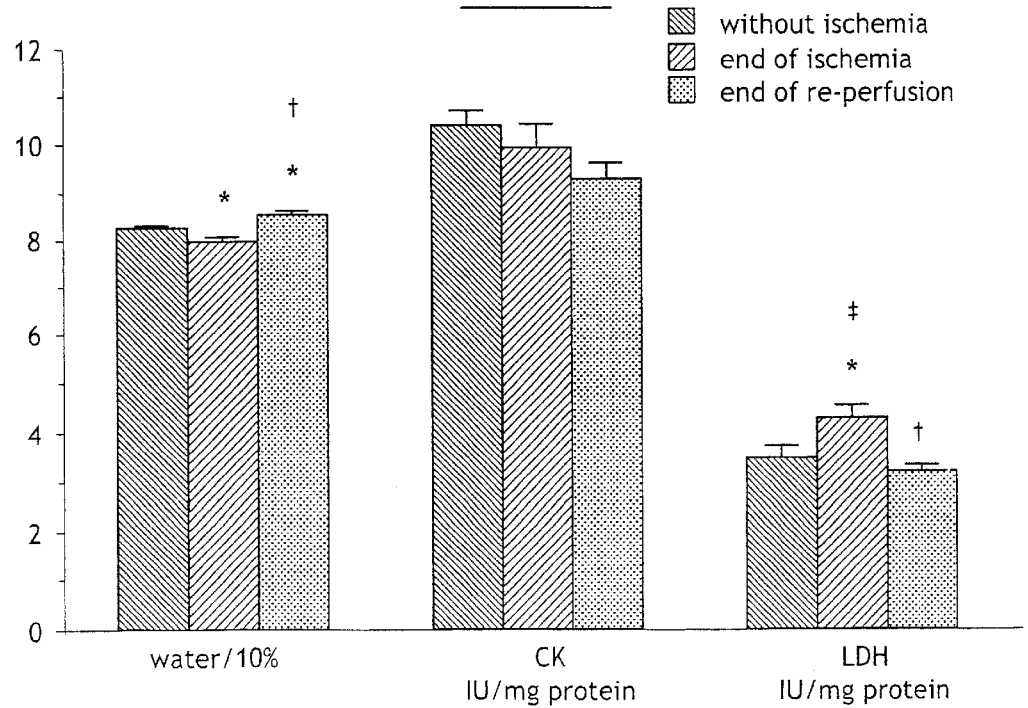

PERFUSION AND/OR PRESERVATION AND/OR RE-PERFUSION SOLUTION DURING ORGAN TRANSPLANT

The invention has as its object a solution for perfusion and/or preservation and/or re-perfusion during organ transplant, especially of the heart.

The preservation period of human hearts is at present 4 hours and a certain number of rejections are still due to deterioration in the condition of the transplanted organ between the time of removal and the moment of implantation in the recipient.

Short-term myocardiac preservation (4 hours) is currently provided by cold storage after cardioplegic arrest. A variety of processes exist however differing by the composition of the solution used, the preservation temperature and the administration protocol. Different solutions for arresting and preserving the heart have been developed to protect the myocardium in cardiac surgery.

The St Thomas solution [Ledingham, S. J. M., Braimbridge, M. V., Hearse, D. J. The St Thomas' Hospital cardioplegic solution: a comparison of the efficacy of two formulations. J. Thorac. Cardiovasc. Surg. (1987) 93: 240–246] has in particular been much used.

Solutions similar to the St Thomas solution have been developed like the Broussais solution [Fabiani, J. N., Ponzio, O., Jebara, V. Myocardiac protection; encycl. Méd. Chir. (Paris, France), Techniques chirurgicales, Thorax, 42511, 10–1989].

More recently experiments have been carried out with the University of Wisconsin (UW) solution [Ledingham, S. J. M., Katayama, O., Lachno, D. R., Yacoub, M. H. Prolonged cardiac preservation. Evaluation of the University of Wisconsin preservation solution by comparison with the St Thomas' solution in the rat. *Circulation* (1990) 82 (Part 2): IV351–8] currently used for other organs (liver, kidney). The use of the UW solution has allowed impressive progress in the preservation of the transplanted organ in renal and hepatic transplantation by significantly increasing the duration of cold ischemia before transplantation.

Certain teams have already reported favourable results by applying the UW solution to the preservation of the cardiac transplant. This solution comprises different protective elements; glutathion and allopurinol, inhibitors of the formation of free radicals from oxygen, water resistant agents (lactobionate and raffinose) and adenosine, a precursor of ATP.

Different solutions directly derived from the UW solution have been developed, yet others take only certain elements of the UW solution (Celsior solution) [Ménasché, P., Termignon, J L., Pradier, F., Grousset, C., Mouas, C. Experimental evaluation of Celsior, a new heart preservation solution. *Eur J. Cardio. Thorac. Surg.* (1994) 8: 207–213].

It has been shown that the University of Wisconsin solution (UW) made it possible to increase the duration of myocardium preservation. This solution comprises different protective elements, glutathion and allopurinol, inhibitors of the formation of free radicals from oxygen, water resistant agents, (lactobionate, raffinose), a precursor of ATP (adenosine). However, this solution has not been specifically developed for the heart and presents various features which are not optimal if not harmful for the heart: 1) the UW solution is characterised for example by a strong concentration in $K^+$ (125 mM) damaging to the cells as it leads to contracture, 2) inorganic phosphate (Pi) is equally present in a strong concentration or it is an inhibitor of numerous ATPases ($Na^+/K^+$ ATPase, $Ca^{2+}$ ATPases) and can thus increase the accumulation in poisonous $Na^+$ and $Ca^{2+}$ in the course of ischemia, 3) it does not comprise any $Ca^{2+}$ and because of this induces a massive influx of $Ca^{2+}$ during re-perfusion, 4) adenosine has numerous effects on the heart and its concentration is not optimised in the solution, 5) the UW solution does not include a certain number of elements whose protective action has been able to be shown in the heart.

Several years ago a cardioplegic solution (solution B20) was developed for short periods of ischemia (2 to 3 hours) [Monique Bernard et al. J Thorac. Cadiovasc Surg 90: 235–242, 1985].

If the needs expressed by the surgeons are considered, only the option of an extension of the duration of preservation to 12 hours or 6 months or more presents any importance. A passage of 4 to 12 hours of preservation in effect corresponds much more to a marginal increase in the duration of ischemia. It presents several advantages; (1) an extension of the geographical area in which the collection of the transplanted organs takes place and thus an increase in the chances of transplantation for a given patient by offering him the possibility to use a removed transplant, from geographically further away, (2) to be able to envisage transplanting by HLA compatibility freeing the necessary time to carry out the best possible donor-recipient matching (such transplants have already shown much better results in terms of survival of the transplant in renal transplantation, than the simple ABO matching currently used for heart transplants), (3) finally, the passage of 4 to 12 hours would leave at least 1 hour for the global non invasive evaluation of the metabolic state of the transplant by magnetic resonance spectroscopy (MRS) and magnetic resonance imaging (MRI) without breach of the chain of sterility inasmuch as the study can be carried out in the preservation bag. Moreover, to date, no known solution allows preservation of the heart for a period longer than 4 hours, and all the more so during a period of 12 hours.

One of the aims of the invention is to suggest a solution of improved quality, used to arrest the heart then preserve it for a duration longer than 4 hours, with a view to transplantation.

One of the other aspects of the invention is to suggest a solution for arrest and preservation of the organ, especially the heart, making it possible to maintain cellular and metabolic integrity of the organs after ischemia.

Another aspect of the invention is to suggest a solution for organ preservation, especially the heart, allowing post-ischemic functional recovery.

The invention concerns a solution for perfusion and/or preservation and/or re-perfusion during organ transplant, especially the heart, characterised in that it contains the following elements:

| | |
|---|---|
| $K^+$ | at a rate of about 4 to about 7 mM, especially about 4 mM |
| $Ca^{2+}$ | at a rate of about 0.2 to about 0.3 mM, especially about 0.25 mM |
| $Mg^{2+}$ | at a rate of about 13 to about 16 mM, especially about 13 mM |
| glutamate | at a rate of 18 to about 22 mM, especially about 20 mM |
| arginine | at a rate of about 2 to about 4 mM, especially about 3 mM |
| adenosine | at a rate of about 0.5 to about 1 mM, especially about 0.5 mM |

The solution developed within the framework of the present invention for the arrest and the preservation of hearts for long term ischemia is such that it induces cardiac arrest with a strong concentration of magnesium rather than potassium. It comprises moreover glutamate (metabolic substrate of ATP in anaerobic) and is characterised by a non zero concentration in $Ca^{2+}$ and a concentration in extracellular type $Na^+$. Different protective agents, (lactobionate, raffinose, glutathion -reduced form-, allopurinol and adenosine) have been added to this solution. As far as certain components (adenosine, butanedione-2,3-monoxime) are concerned, research on the optimal concentration has been carried out. Recent work has underlined the importance of endothelial dysfunction in the damage linked to the ischemia-re-perfusion sequence. Because of this fact, L-arginine was included, precursor of NO, in the preservation solution.

By solution for re-perfusion during organ transplantation, is designated a solution useable during the transplant of an organ, to make the transplanted organ go from an ischemic state to the cardioplegic state.

According to an advantageous method of implementation, the solution of the invention does not contain butanedione 2.3-monoxime.

According to an advantageous method of implementation, the invention solution contains at least one water resistant agent chosen from lactobionic acid, mannitol and raffinose.

By order of preference, the water resistant agent is chosen from: lactobionic acid, mannitol and raffinose.

According to another advantageous method of implementation, the invention solution contains at least one agent to trap free radicals, chosen notably from glutathion (reduced form), allopurinol, or mannitol.

According to another advantageous method of implementation, the invention solution contains the following elements:

| | |
|---|---|
| $K^+$ | at a rate of about 4 to about 7 mM, especially about 4 mM |
| $Ca^{2+}$ | at a rate of about 0.2 to about 0.3 mM, especially about 0.25 mM |
| $Mg^{2+}$ | at a rate of about 13 to about 16 mM, especially about 13 mM |
| glutamate | at a rate of 18 to about 22 mM, especially about 20 mM |
| arginine | at a rate of about 2 to about 4 mM, especially about 3 mM |
| adenosine | at a rate of about 0.5 to about 1 mM, especially about 0.5 mM | at least one water resistant agent,
at least one agent trapping free radicals
Osmolarity 340 mOsm
pH 7.4

According to another advantageous method of implementation, the invention solution contains the following elements:

| | |
|---|---|
| $K^+$ | of about 4 to about 7 mM, |
| $Ca^{2+}$ | of about 0.2 to about 0.3 mM, |
| $Na^+$ | of about 108 to about 132 mM |
| $Mg^{2+}$ | of about 13 to about 16 mM, |
| glutamate | of about 18 to about 22 mM, |
| arginine | of about 2 to about 4 mM, |
| adenosine | of about 0.5 to about 1 mM |
| mannitol | of about 27 to about 33 mM |
| allopurinol | of about 0.9 to about 1.1 mM |
| glutathion (reduced form) | of about 2.7 to about 3.3 mM |
| raffinose | of about 25 to about 35 mM |
| lactobionic acid | of about 80 to about 120 mM |
| pH | of about 7.2 to about 7.4 |
| osmolarity | of about 330 to about 360 mOsm |

In the solution of the invention, $Na^+$ is in the form NaOH, $K^+$ is in the form KCl and $KH_2PO_4$, favourably at the rate of 2 to about 3.5 mM KCl and about 2 to about 3.5 mM $KH_2PO_4$, $Ca^{2+}$ is in the form of $CaCl_2$, $2H_2O$ and $Mg^{2+}$ is in the form of $MgCl_2$, $6H_2O$.

The invention solution is such that it allows the preservation of organs, especially the heart for a duration of at least 12 to 15 hours and particularly for at least 12 hours.

The invention equally concerns a solution as described above, to maintain the cellular and metabolic integrity of the organ after ischemia, this integrity can be detected by measuring the activity of at least one of the following enzymes: lactate dehydrogenase, creatine kinase and/or by measurement of at least one of the following metabolites: purines, nucleotides especially adenylic nucleotides, inosine monophosphate, adenosine triphosphate, amino acids, inorganic phosphate, lactate, phosphocreatine.

The invention equally concerns a solution such as is described above, to ensure functional post ischemic recovery, this functional recovery able to be measured by the measurement of at least one of the following hemodynanic parameters: coronary flow, the developed pressure, the cardiac frequency, and the diastolic pressure., The quality of preservation is measured by studying the functional and metabolic parameters as well as the measurement of cellular integrity.

The measured functional parameters are:
the developed pressure,
the diastolic pressure,
the cardiac frequency, these three parameters being measured thanks to a small balloon placed in the left ventricle on which the heart contracts; the small balloon is linked to an amplifier (Statham P23dB) which is connected to a recorder,
and the coronary flow (measurement of the discharge coming from the heart during a given time).

The functional parameters are measured during the control period and during the period of re-perfusion.

The metabolic parameters measured are:
inorganic phosphate,
adenosine triphosphate,
phosphocreatine, and
intracellular pH.

The acquisition of RMN spectrums of P-31 makes it possible to follow the levels of Pi (inorganic phosphate), ATP (adenosine triphosphate), PCr (phosphocreatine) as well as the intracellular pH (ATP and PCr=high energy phosphorous components). The spectrums are acquired throughout the entire duration of the experiment (control, ischemia, re-perfusion).

The adenylic nucleotides, inosine monophosphate and the purines are measured in the frozen hearts at the end of the experiment; this measurement is additional to the results obtained from the RMN spectrums of the P-31.

The amino acids are measured in the frozen hearts at the end of the experiments. They play an important role in the metabolism and maintenance of cardiac cellular function. They are depleted during ischemia and re-perfusion. The size of this depletion is a reflection of the deterioration of the heart.

The inorganic phosphate (Pi) and the purines are measured in the discharge coming from the heart and are thus only measured during the periods of perfusion (control and re-perfusion). The Pi and the purines are accumulated during ischemia and come out of the heart at the moment of re-perfusion, representing a loss of precursors for the synthesis of the high energy compounds.

The lactate in the discharges (control and re-perfusion) is evaluated as an indicator of the metabolism of energy in anaerobia.

Parameters reflecting cellular integrity.

The leakage of creatine kinase (CK) in the discharges indicates cellular damage.

The quantities of creatine kinase (CK) and lactate dehydrogenase (LDH) in the frozen hearts at the end of the experiment equally represent an indicator of cellular integrity.

The myocardiac water content equally reflects cellular integrity.

In order to highlight the importance presented by the invention solution, this has been compared, with the aid of a large number of parameters and in comparison to the protection provided, to reference solutions that are the St Thomas solution and the UW solution, used in the preservation of cardiac transplants. A comparison with the Broussais and Celsior solutions, used in certain French transplant centres has equally been done. The results show that the invention solution permits greater protection than that given by the other solutions:

St Thomas, UW, Broussais, Celsior (cf.figures).

The invention solution can be used during all the phases of a transplant:

1) to stop the heart of the donor (cardioplegic solution),
2) to preserve the heart (hypothermic storage, transportation),
3) during re-implantation in the recipient.

The invention solutions can be prepared in the following manner: the different constituents are dissolved and diluted in distilled water, the pH is adjusted to 7.4 with NaOH. The solution is filtered on 0.21 µm. The apyrogenic and sterile solution is prepared and kept away from oxygen in the air.

ABREVIATIONS USED (Figures, Text)

ATP=adenosine triphosphate
ADP=adenosine diphosphate
AMP=adenosine monophosphate
PCr=phosphocreatine
Pi=inorganic phosphate
LDH=lactate dehydrogenase
CK=creatine kinase
HPLC=high pressure liquid chromatography
MRS=magnetic resonance spectroscopy
EDP=diastolic pressure
dP=developed pressure
CF=coronary flow
RPP="rate pressure product"=cardiac frequency× developed pressure
NAD=nicotinamide adenine dinucleotide In the following, a solution conforming to the invention, useable for isolated hearts, presents the following composition:

KCl (2 mM), $KH_2PO_4$ (2 mM), $CaCl_2$ (0.25 mM), $MgCl_2$ (13 mM), NaOH (120 mM), arginine (2 mM), glutamate (20 mM), adenosine (0.5 mM), lactobionic acid (100 mM), raffinose (30 mM), glutathion (3 mM), allopurinol (1 mM), mannitol (30 mM).

A solution in accordance with the invention, useable for heterotopic transplantation, has the following composition:

KCl (2 mM), $KH_2PO_4$ (2 mM), $CaCl_2$ (0.25 mM), $MgCl_2$ (13 mM), NaOH (120 mM), arginine (3 mM), glutamate (20 mM), adenosine (0.5 mM), lactobionic acid (100 mM), raffinose (30 mM), glutathion (3 mM), allopurinol (1 mM), mannitol (30 mM).

A solution with a composition similar to that of the invention, not containing arginine, is named as "CRMBM" in the following and has the following composition:

KCl (2 mM), $KH_2PO_4$ (2 mM), $CaCl_2$ (0.25 mM), $MgCl_2$ (13 mM), NaOH (120 mM), glutamate (20 mM), adenosine (0.5 mM), lactobionic acid (100 mM), raffinose (30 mM), glutathion (3 mM), allopurinol (1 mM), mannitol (30 mM).

DESCRIPTION OF THE DIAGRAMS

FIG. 1 shows the experimental protocol used in examples 1 and 2 described hereafter.

In FIG. 1, ①②③④ and ⑤ have the following meaning:

① corresponds to the control (20 mn, 37° C.);
   PCr, ATP, Pi, pHi are measured by spectrums P-31 and Pi, CK, purines and lactate in the discharges.
② corresponds to ischemia (6 hours or 8 hours or 12 hours at 4° C.)
   PCr, ATP, Pi, pHi are measured by spectrums P-31.
③ corresponds to re-perfusion for 1 hour at 37° C.;
   PCr, ATP, Pi, pHi are measured by spectrums P-31
   Pi, CK, lactate and purines are measured in the discharges during re-perfusion;

The nucleotides, purines, amino acids and the water content after freezing the hearts are then measured.

④ corresponds to the cardioplegic stage (50 ml).
⑤ corresponds to the freezing of the hearts.

FIG. 2 shows experimental protocol No. 1 (see comparative example 3).

In FIG. 2, ① ② ③ and ④ have the following meanings:

① control (20 mn, 37° C.).
② ischemia (12 hours, 4° C.).
③ re-perfusion (1 hour, 37° C.).
④ corresponds to the cardioplegic stage (50 ml).

FIGS. 3A and 3B show, within the framework of protocol No.1, the kinetics of the hemodynamic parameters during re-perfusion with the aid of the St Thomas solution (indicated by black squares), of the Broussais solution (indicated by white squares), of the UW solution (indicated by black circles), of the CRMBM solution (indicated by white circles) respectively.

*p<0.0001 with regard to the Broussais solution, p<0.001 with regard to the UW and St Thomas solutions
†p<0.0001 with regard to the Broussais solution, and UW, p<0.01 with regard to the St Thomas solution.

Figure 1:
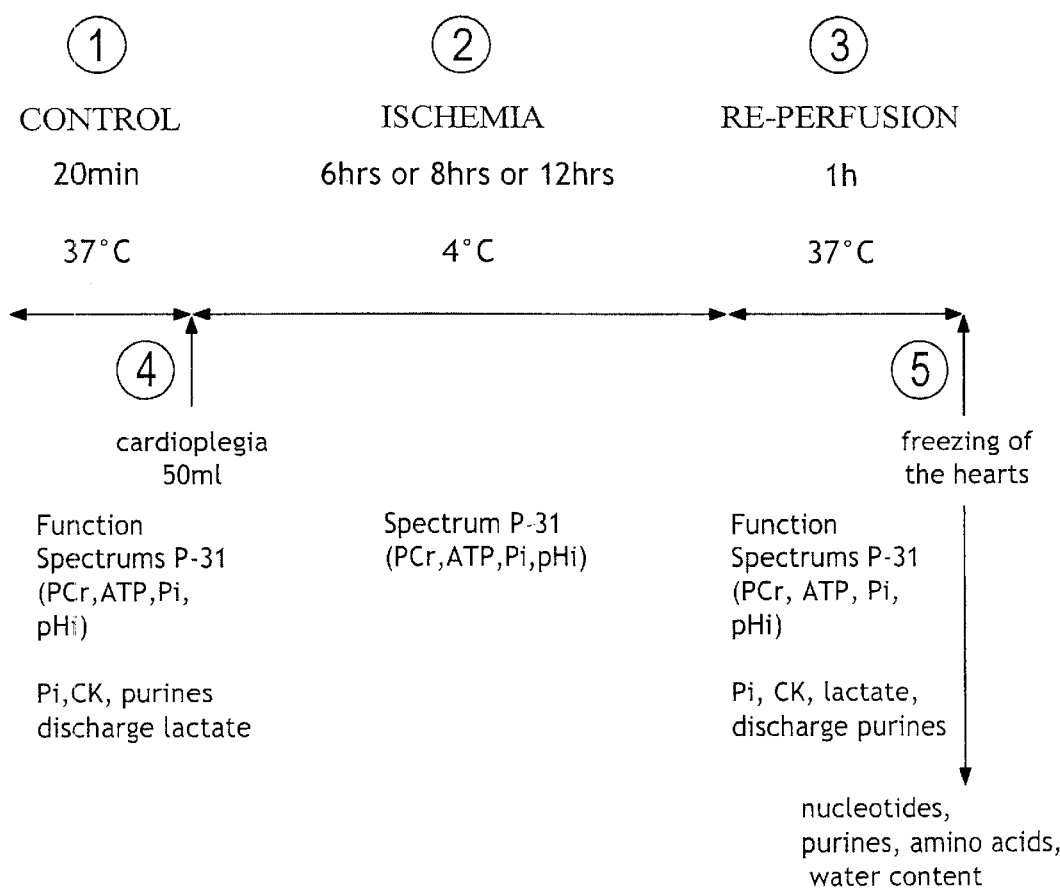
Figure 2:
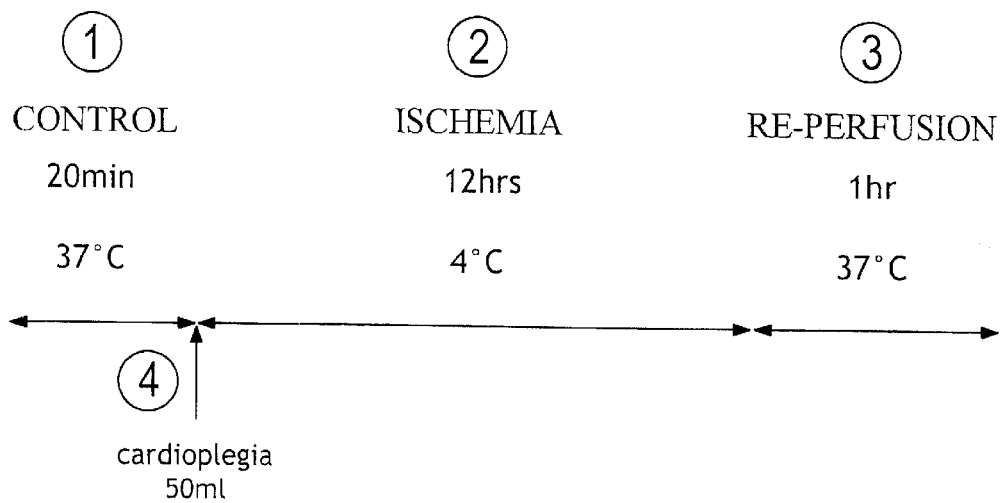
Figure 3A:
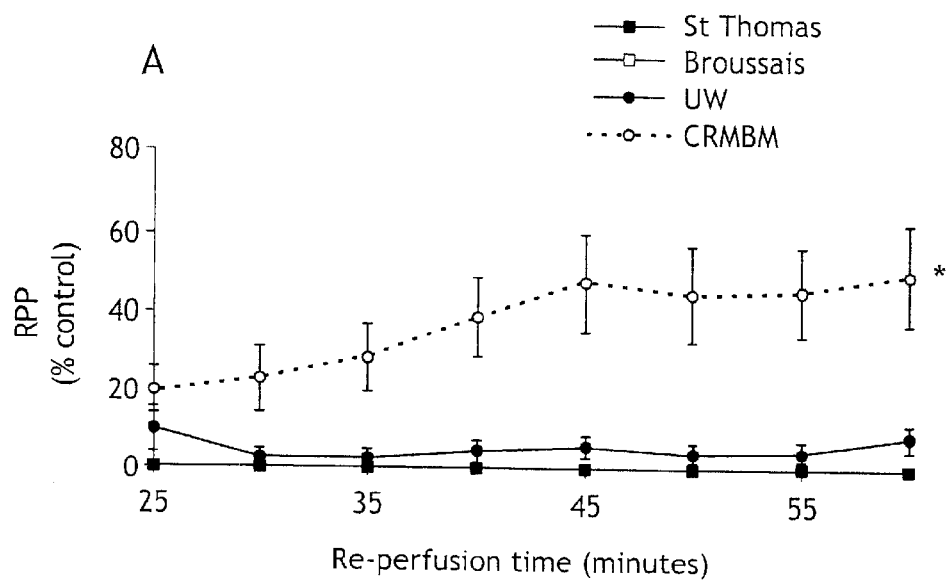
FIG. 3A shows the product of the cardiac frequency by the developed pressure (RPP) (percentage in comparison to the control) expressed in function of re-perfusion time (in minutes).
Figure 3B:
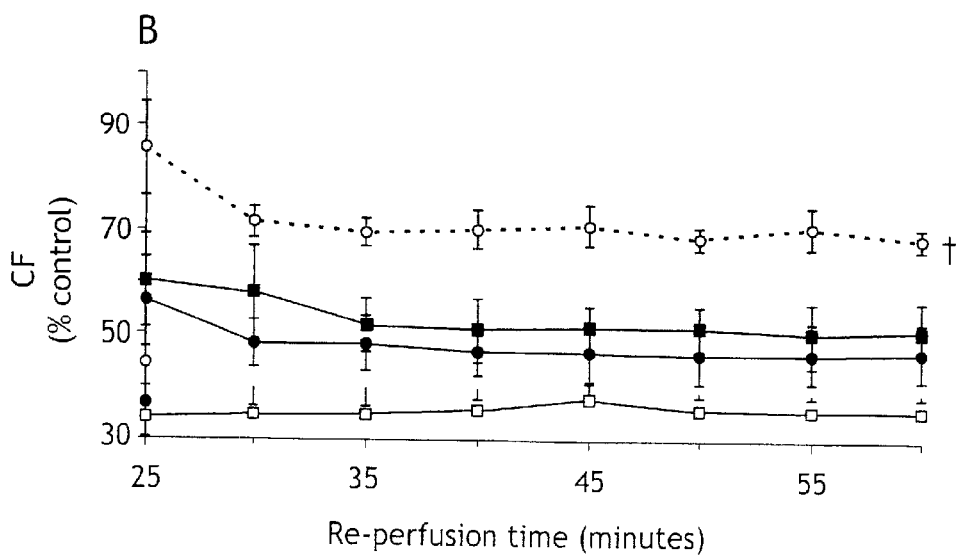
FIG. 3B represents the coronary flow (CF) (percentage in comparison to the control) expressed in function of the re-perfusion time in minutes.
Figure 4A:
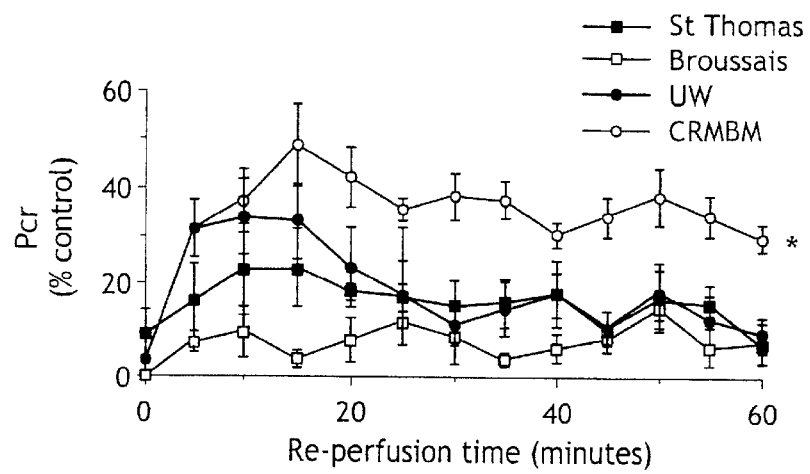
FIG. 4A shows, within the framework of protocol No. 1, the variation of phosphocreatine (PCr) (percentage in comparison to the control) in function of the re-perfusion time (expressed in minutes).
Figure 4B:
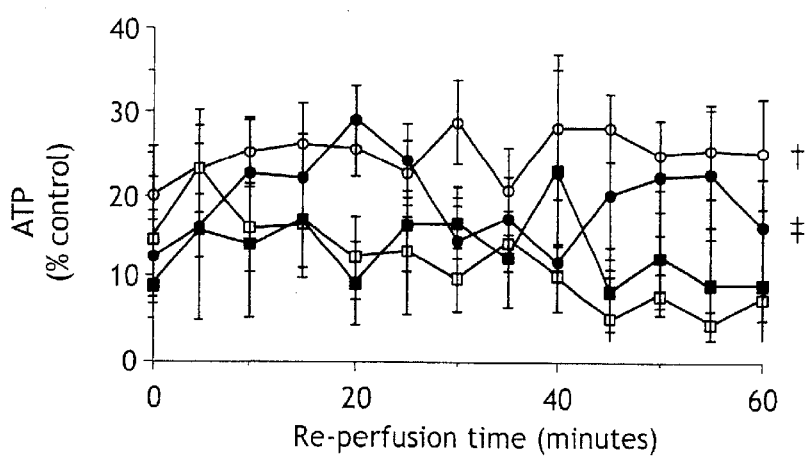
FIG. 4B shows, within the framework of protocol No. 1, the variation of adenosine triphosphate (ATP) (percentage in comparison to the control) in function of the re-perfusion time (expressed in minutes).
Figure 4C:
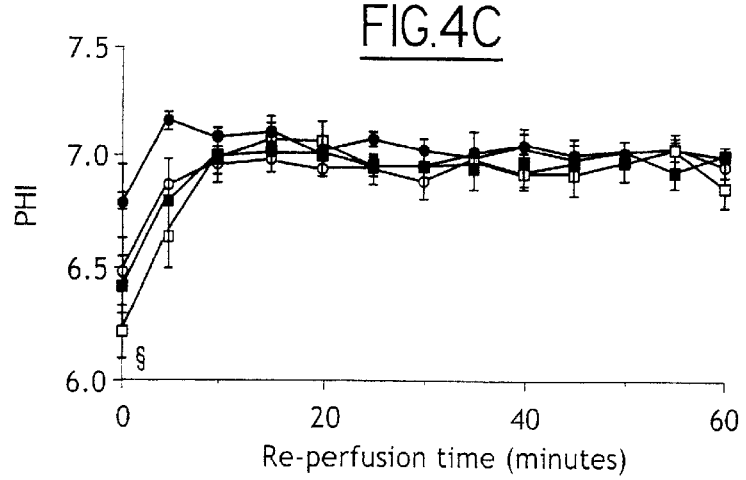
FIG. 4C shows, within the framework of protocol No. 1, the variation of intracellular pH (pHi).

In FIGS. 4A, 4B and 4C, the time 0 corresponds to the end of ischemia.

In FIGS. 4A and 4B and 4C, the St Thomas solution (indicated by black squares), the Broussais solution (indicated by white squares), the UW solution (indicated by black circles), the CRMBM solution (indicated by white circles are shown respectively.

In FIGS. 4A, 4B, 4C

*$p<0.05$ with regard to the UW solution, $p<0.001$ with regard to the Broussais and St Thomas solutions, †$<0.01$ with regard to Broussais solution, $p<0.01$ with regard to the St Thomas solution, ‡$<0.0001$ with regard to the Broussais solution. $p<0.05$ with regard to the UW solution.

Figure 5:
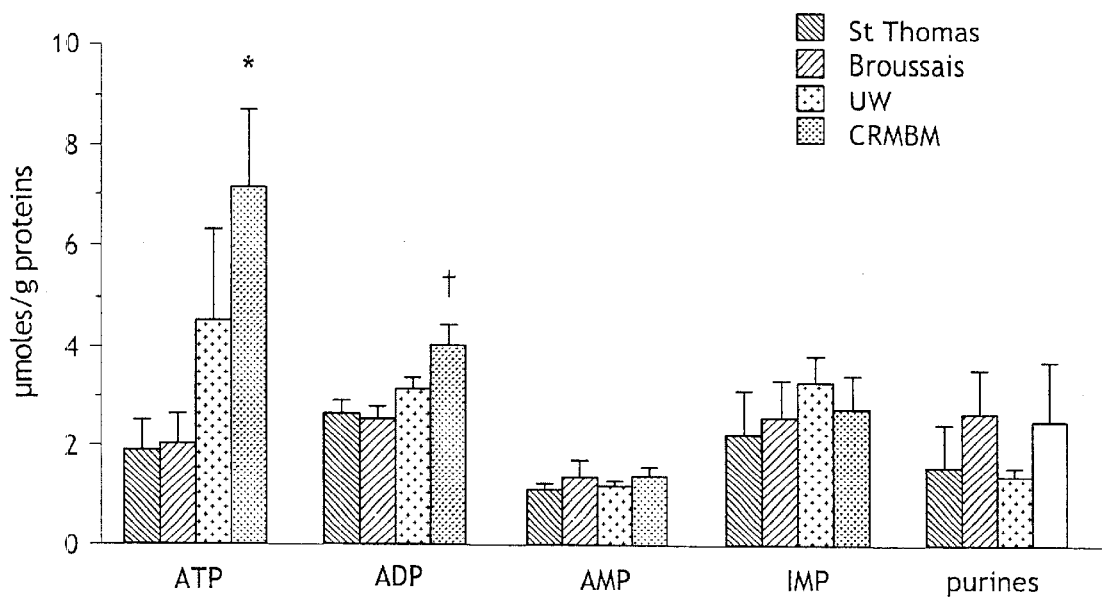

FIG. 5 shows, within the framework of protocol No. 1, the content in adenylic nucleotides (ATP=adenosine triphosphate, ADP=adenosine diphosphate, AMP=adenosine monophosphate, IMP (inosine monophosphate), and purines, in the frozen hearts at the end of ischemia). These contents are expressed in micromoles per gram of proteins.

The St Thomas solution is represented in black, the Broussais solution is represented in black and white hatching. The UW solution is represented by perpendicular dotted lines and the CRMBM solution, of a similar composition of that of the invention, is represented in grey.

In FIG. 5

*$p<0.05$ with regard to the Broussais and St Thomas solution,

†$p<0.05$ with regard to the Broussais solution.

Figure 6:
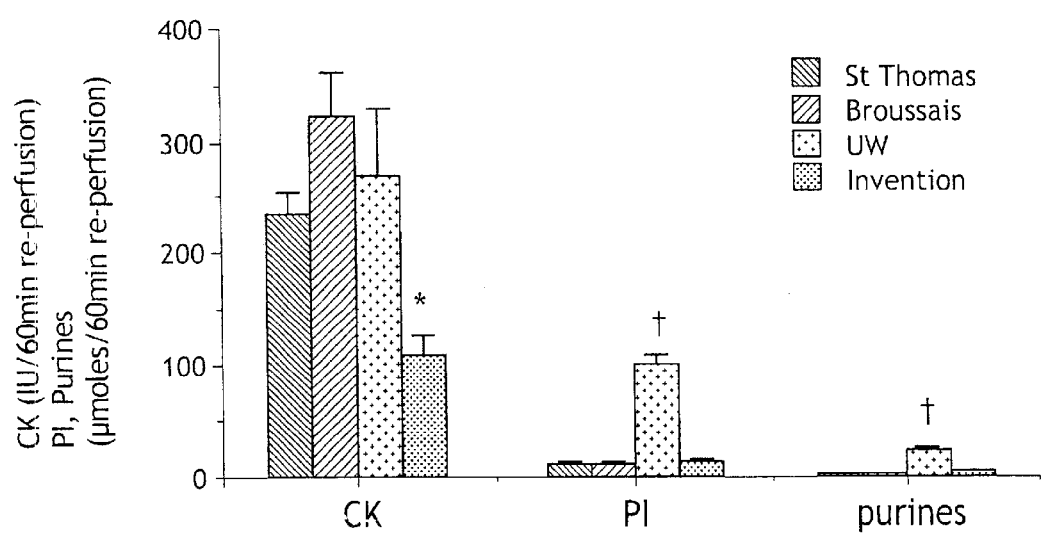

FIG. 6 represents, within the framework of protocol No.2, the metabolites in the coronary discharges during re-perfusion. These metabolites are:

CK (creatine kinase) expressed in international units per 60 mn of re-perfusion, Pi (inorganic phosphate) expressed in micromoles per 60 minutes of re-perfusion, purines expressed in micromoles per 60 minutes of re-perfusion.

In FIG. 6

*$p<0.0001$ with regard to the St Thomas and UW solutions, $p<0.001$ with regard to the Broussais solution, †$p<0.0001$ with regard to the invention, Broussais and St Thomas solutions.

Figure 7A:
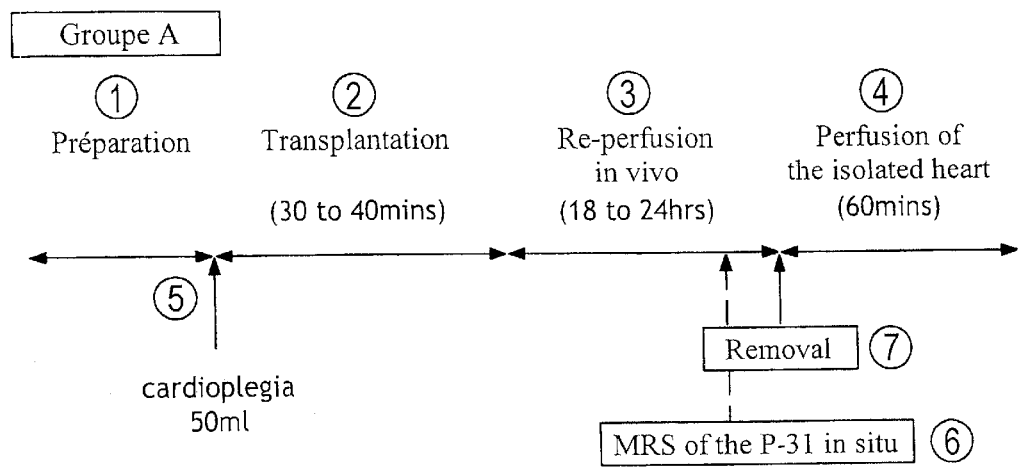
Figure 7B:
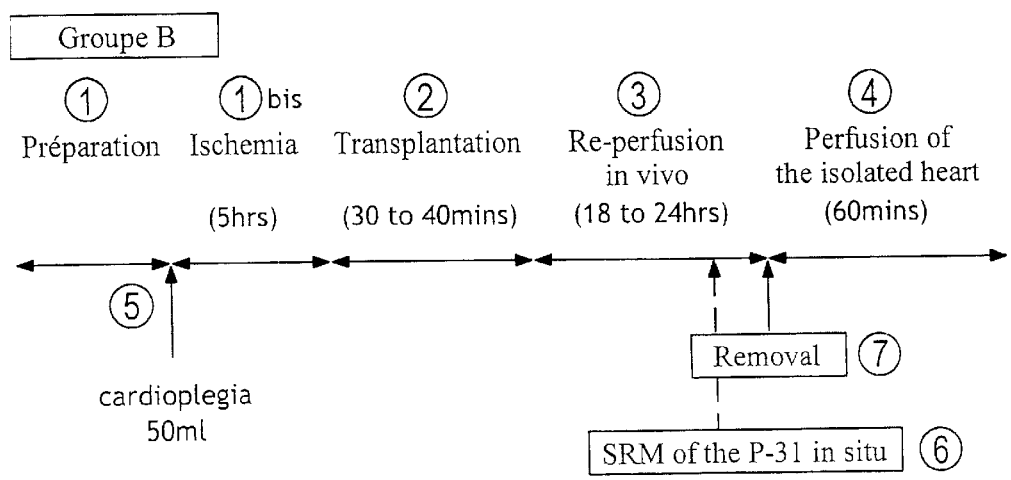

FIGS. 7A and 7B correspond to experimental protocol No.2.

FIG. 7A corresponds to group A (described in protocol No.2).

FIG. 7B corresponds to group B (described in protocol No.2).

In FIGS. 7A and 7B, ①②③④⑤⑥⑦ and ① bis have the following meanings:

① preparation ① bis ischemia (5 hrs)

② transplantation (30 to 40 mn)

③ re-perfusion in vivo (18 to 24 hours).

④ perfusion of the isolated heart (60 mn).

⑤ cardioplegia (50 ml).

⑥ SRM of the P-31 in situ

⑦ removal of the heart.

Figure 8A:
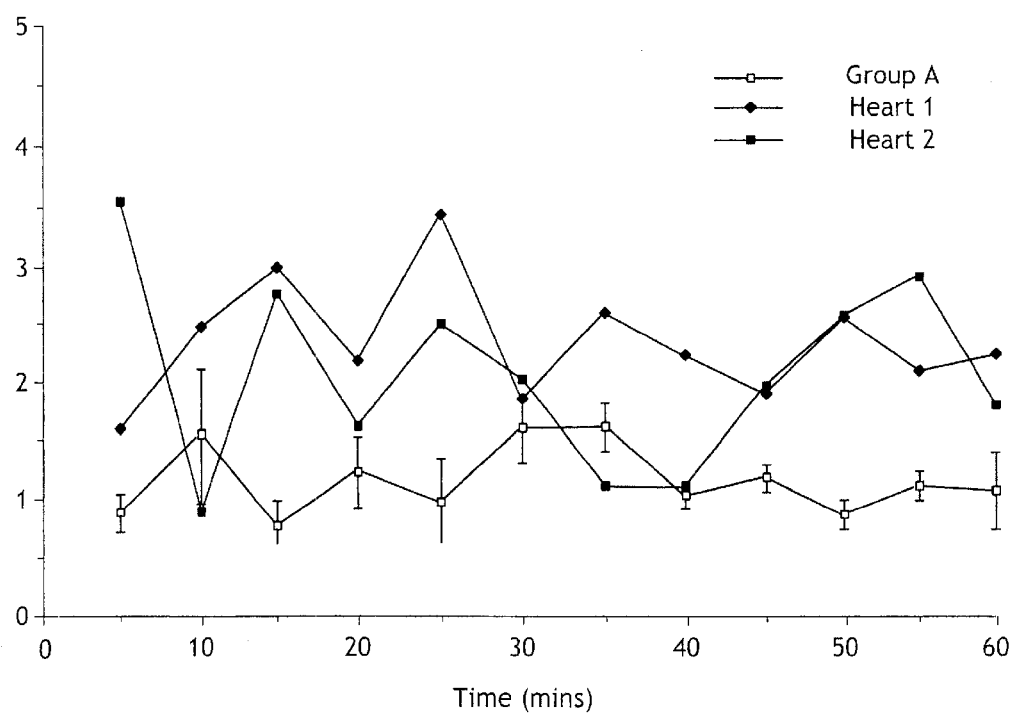

FIG. 8A corresponds, within the framework of protocol No.2, to the variation of the PCr/ATP ratio expressed in function of time (in minutes).

Figure 8B:
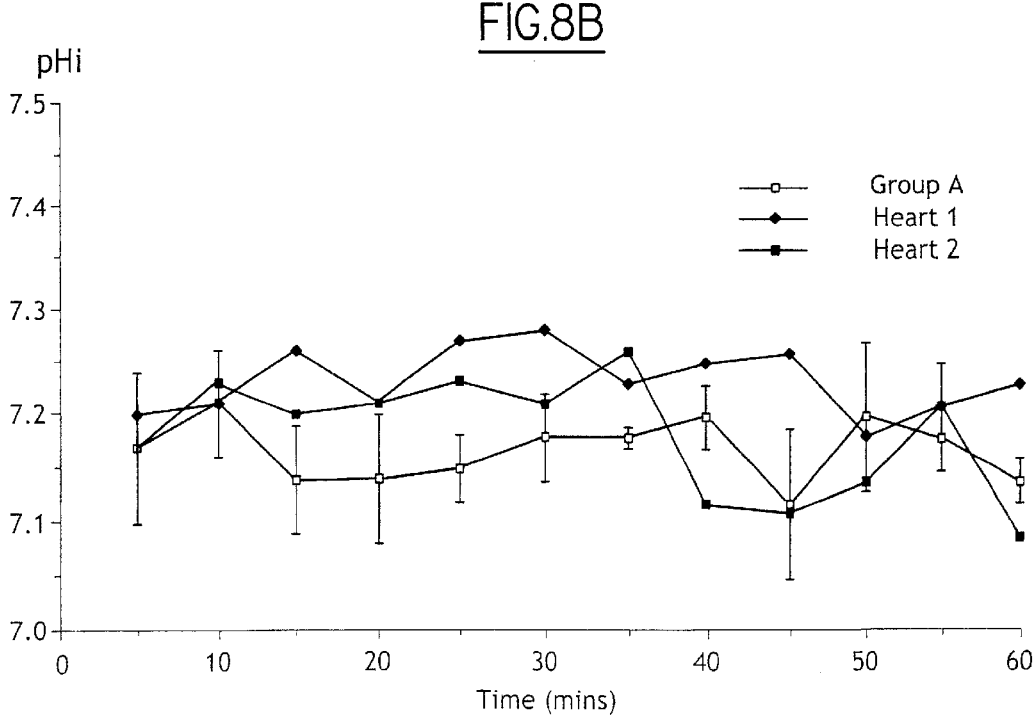

FIG. 8B corresponds to the variation of intracellular pH (pHi) expressed in function of time (in minutes).

Group B corresponds to the heart 1 and heart 2 together.

The results of group A correspond to the average of 4 experiments.

The results of group B are represented by 2 experiments (heart 1 and heart 2).

The curves with white squares comprising a dot in their centre, correspond to group A, the curves with black diamonds correspond to heart I (group B) and the curves comprising white squares correspond to heart 2 (group B).

FIG. 9 shows experimental protocol No.3.

In FIG. 9, ① ② ③ and ④ have the following meanings:

① control (20 mn, 37° C.).

② ischemia (8 hours, 4° C.).

③ re-perfusion (1 hour, 37° C.).

④ cardioplegia (50 ml).

Figure 10A:
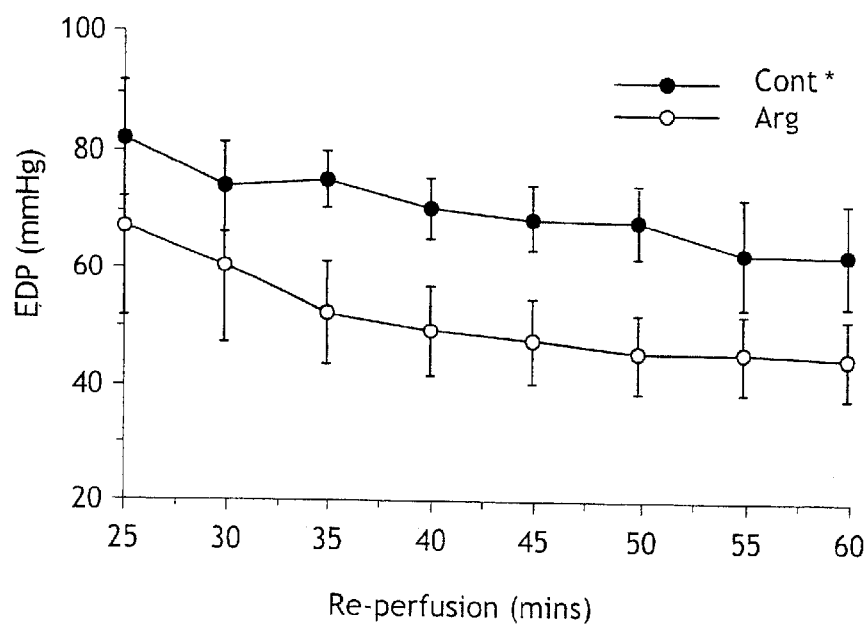

FIG. 10A corresponds, within the framework of protocol No.3, to the variation of diastolic pressure (EDP) (in mm of Hg), expressed in function of re-perfusion time (in minutes).

Figure 10B:
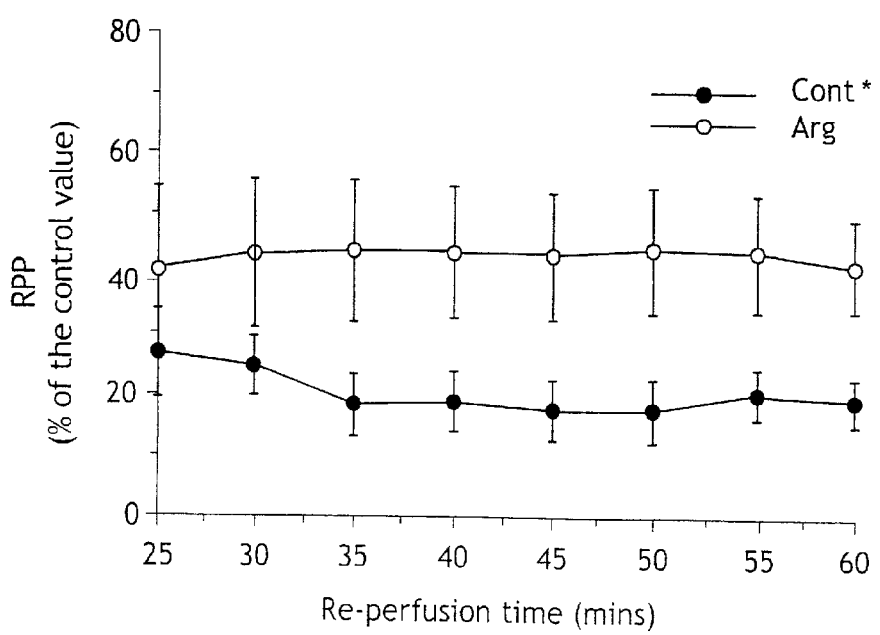

FIG. 10B corresponds, within the framework of protocol No.3, to the variation of the product of the developed pressure by the cardiac frequency (RPP) (expressed as a percentage of the control value) in function of the re-perfusion time (in minutes).

In FIGS. 10A and 10B the curves comprising white circles correspond to the presence of arginine and the curves comprising black circles correspond to the control solution.

$p<0.0001$ within the framework of the curve corresponding to the control solution containing arginine.

Figure 11:
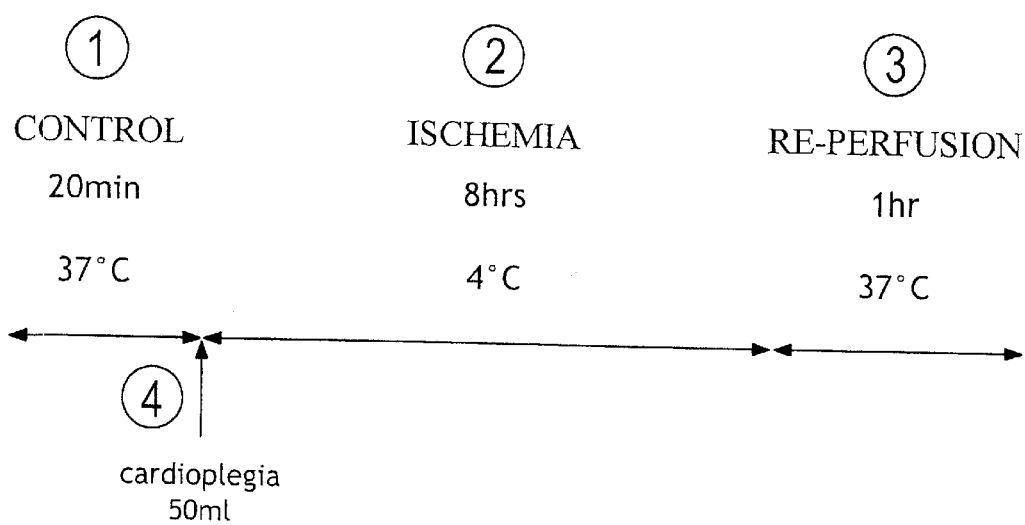

FIG. 11 corresponds to experimental protocol No.4.

In FIG. 11, ① ② ③ and ④ have the following meanings:

① control (20 mn, 37° C.).

② ischemia (8 h, 4° C.).

③ re-perfusion (1 h, 37° C.).

④ cardioplegia (50 ml).

Figure 12:
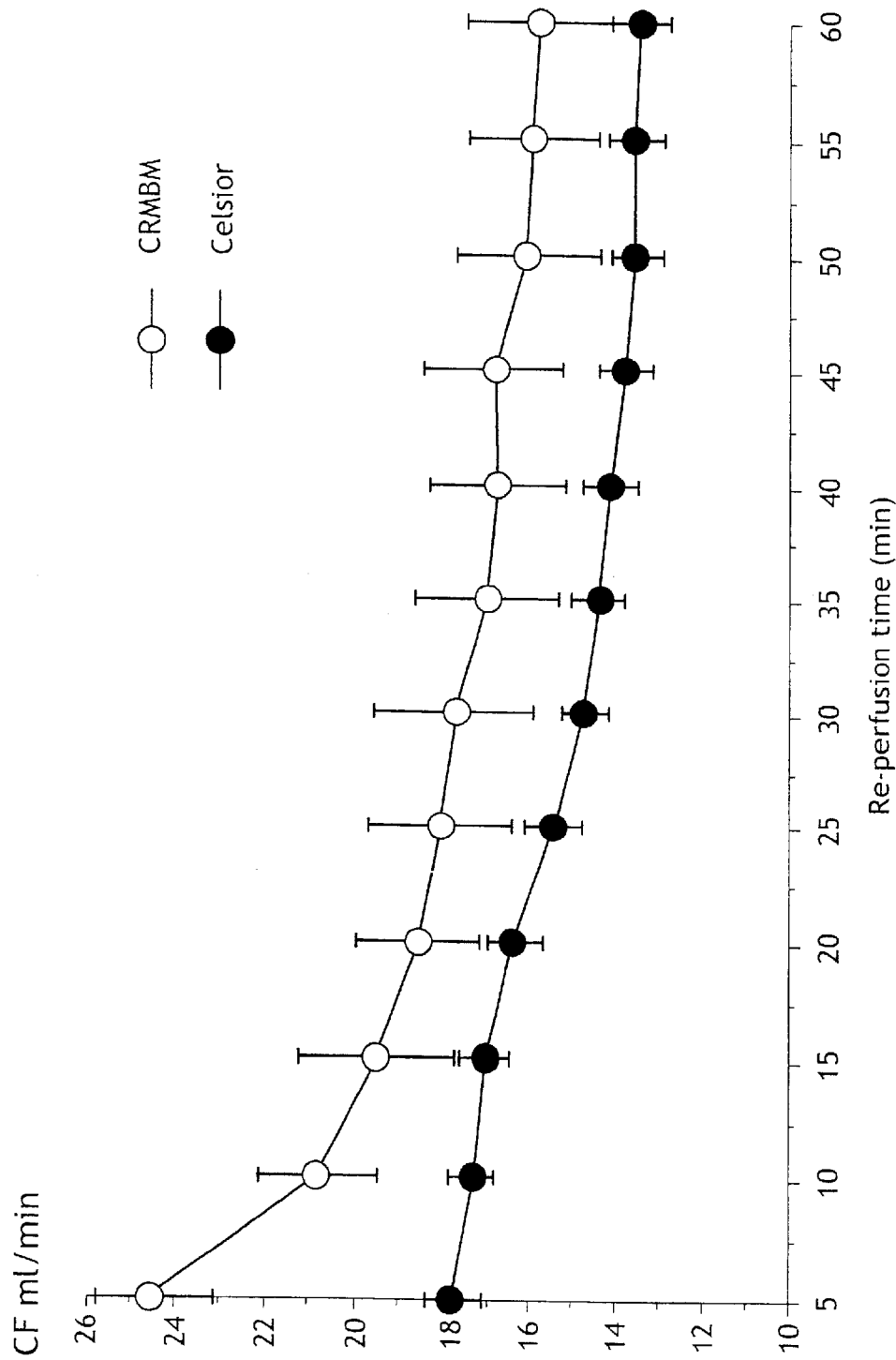

FIG. 12 corresponds, within the framework of protocol No.4, to the variation in the coronary flow (CF) (expressed in ml/mn) in function of the re-perfusion time (in minutes).

The curve with black circles corresponds to the Celsior solution and the curve with white circles corresponds to the invention solution.

Figure 13:
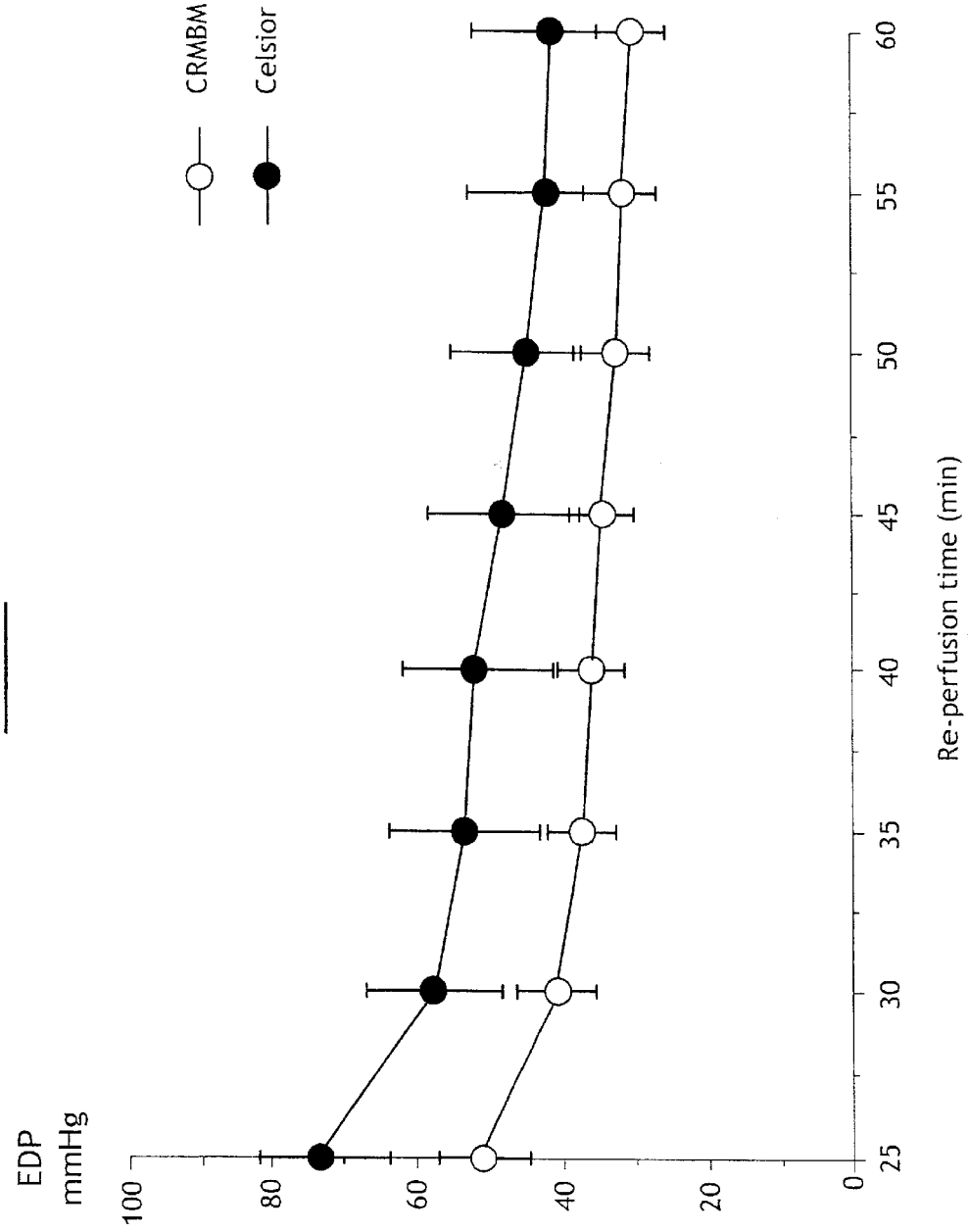

FIG. 13 corresponds, within the framework of protocol No.4, to the variation of diastolic pressure (EDP) (expressed in mm/Hg) in function of the re-perfusion time (in minutes).

The curve with black circles corresponds to the Celsior solution and the curve with white circles corresponds to the invention solution.

Figure 14:
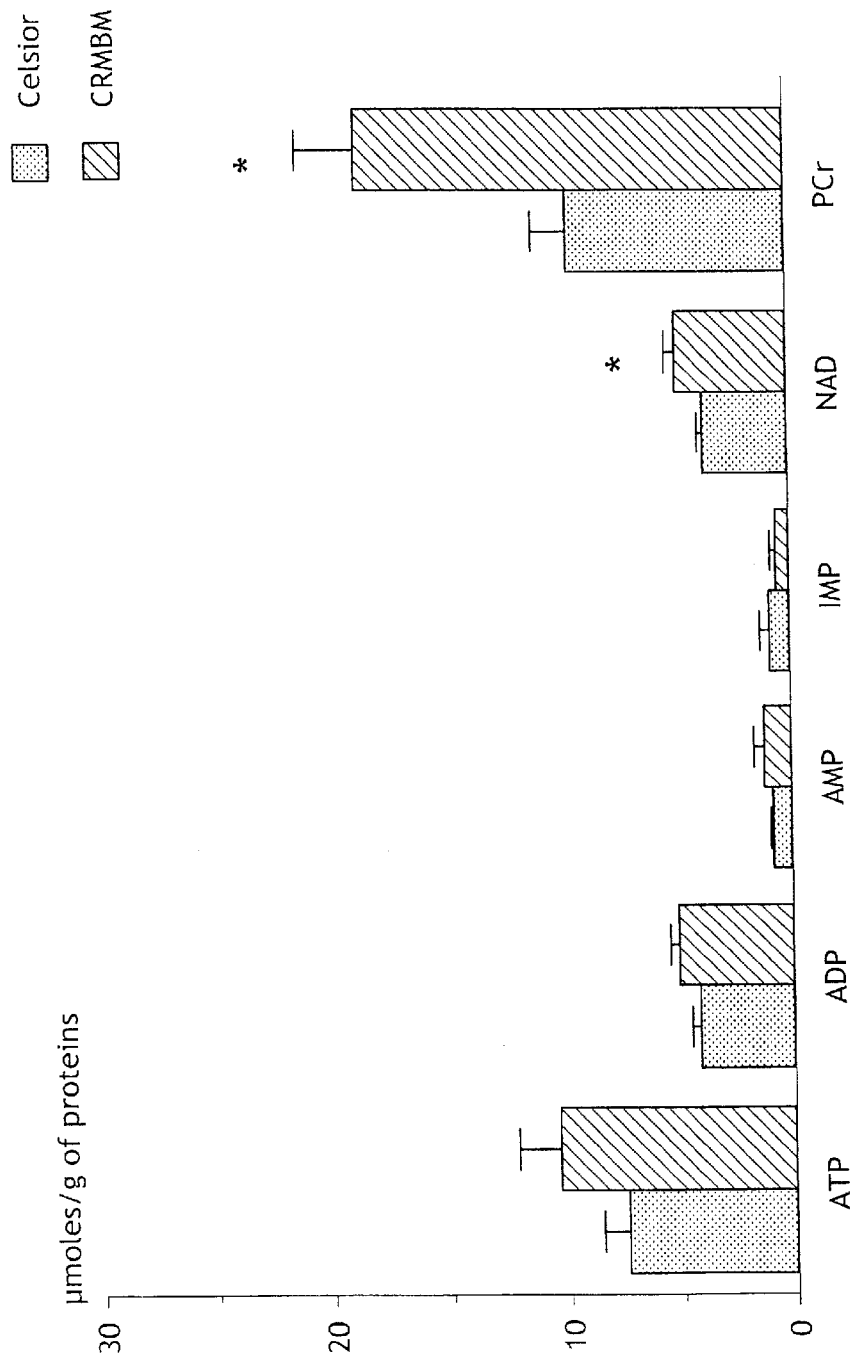

FIG. 14 corresponds, within the framework of protocol No.4, to the proportion of nucleotides in the frozen hearts at the end of re-perfusion. The proportion of ATP (adenosine triphosphate), ADP (adenosine diphosphate), AMP (adenosine monophosphate), IMP (inosine monophosphate), NAD (nicotinamide adenine dinucleotide), PCr (phosphocreatine), is thus expressed in micromoles per gram of protein.

The Celsior solution is represented in black and the invention solution is represented by hatching.

p<0.05 within the framework of the invention solution with regard to the Celsior solution.

Figure 15:
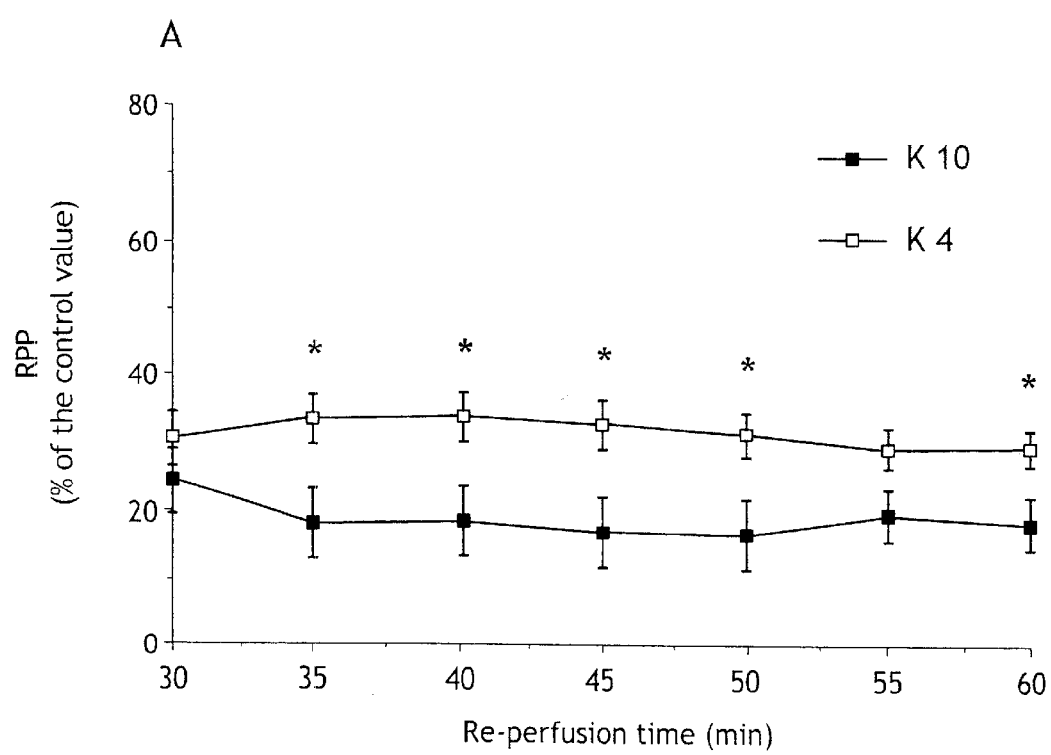

FIG. 15 represents, within the framework of the experimental protocol used in example 3 hereafter, the percentage of recovery of myocardiac function, expressed in the form of the product of the pressure developed by the cardiac frequency (RPP), in function of the re-perfusion time (in minutes) in the presence of 4 mM or 10 mM of potassium.

The preservation solution containing 4 mM of potassium is indicated by white squares, and that containing 10 mM of potassium is indicated by black squares.

In FIG. 15, *p<0.05 with regard to the solution containing 10 mM of potassium.

FIGS. 16A and 16B show, within the framework of the experimental protocol used in example 3, the variation of ATP in function (1) of the period of ischemia (expressed in hours) (FIG. 16A), and (2) of the re-perfusion time (expressed in minutes) (FIG. 16B), with of 4 mM or 10 mM of potassium respectively.

In FIG. 16A, the time 0 corresponds to the start of ischemia, and the negative values correspond to the pre-ischemic recording (perfusion control).

In FIG. 16B, the time 0 corresponds to the end of ischemia and to the start of re-perfusion.

In FIGS. 16A and 16B, the preservation solution containing 4 mM of potassium is indicated by white squares, and the one containing 10 mM of potassium is indicated by black squares.

FIGS. 17A and 17B show, within the framework of experimental protocol 3 (corresponding to 8 hours of ischemia and 60 minutes of re-perfusion), the content in amino acids (ASP=Aspartic acid, GLU=Glutamic acid, SER=Serine, ASN=Asparagine, GLY=Glycine, GLN=Glutamine, TAU=Taurine protein, ALA=Alanine, ARG=Arginine, LYS=Lysine) in the hearts without ischemia, at the end of ischemia, and at the end of re-perfusion (1) for the hearts without arginine (FIG. 17A), and (2) for the hearts with arginine (FIG. 17B) respectively.

The abbreviation "GLU/2" represents the concentration of glutamine divided by 2, and "TAU/5" the concentration of taurine divided by 5 (this is because of problems of scale, in order to be able to put all the amino acids on the same graph).

The contents are expressed in micromoles per gram of proteins.

In FIGS. 17A and 17B, the black histogram represents the amino acid content in the hearts without ischemia, the histogram in hatched black and white lines the amino acid content in the hearts at the end of ischemia, the grey histogram the amino acid content in the hearts at the end of re-perfusion.

In FIGS. 17A and 17B:
  *p<0.05 with regard to the hearts without ischemia,
  †p<0.05 with regard to the hearts at the end of ischemia.
In FIG. 17B:
  ‡p<0.05 with regard to the control group.

FIGS. 18A and 18B show from left to right, within the framework of experimental protocol 3, the water (expressed in %), creatine kinase (CK) and dehydrogenase lactate (LDH) content (expressed in international units per mg of protein) in the hearts without ischemia, at the end of ischemia and at the end of re-perfusion (1) for the solutions not containing arginine (FIG. 18A) and (2) for the solutions according to the invention containing arginine (FIG. 118B) respectively.

In FIGS. 18A and 18B, the black histogram represents the water, CK and LDH content in the hearts without ischemia, the histogram with black and white hatching the water, CK and LDH content in the hearts at the end of ischemia, the grey histogram the water, CK and LDH content in the hearts at the end of re-perfusion.

In FIGS. 18A and 18B:
  *p<0.05 with regard to hearts without ischemia,
  †p<0.05 with regard to hearts at the end of ischemia.

Figure 19A:
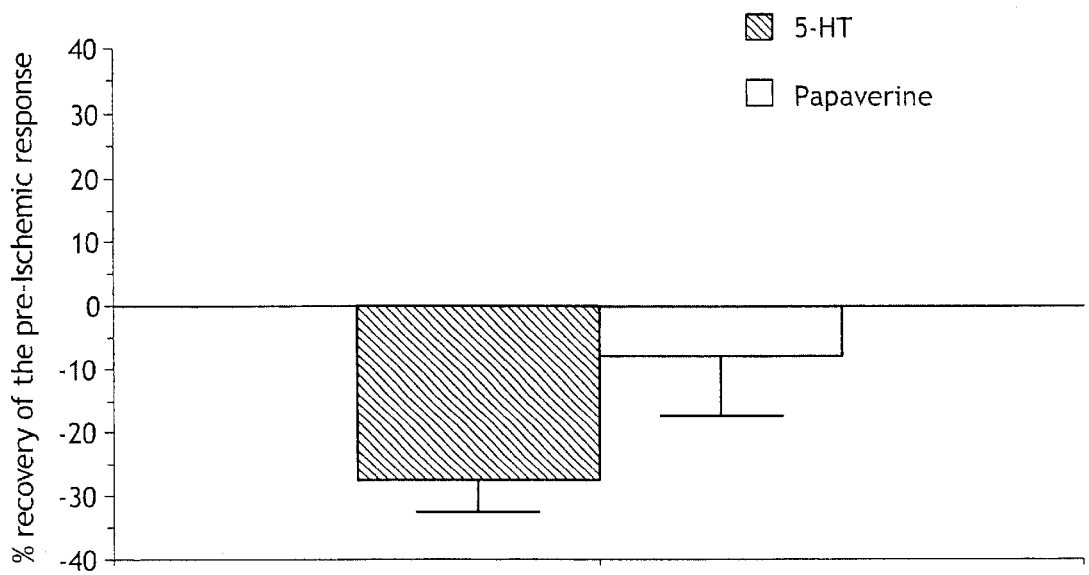
Figure 19B:
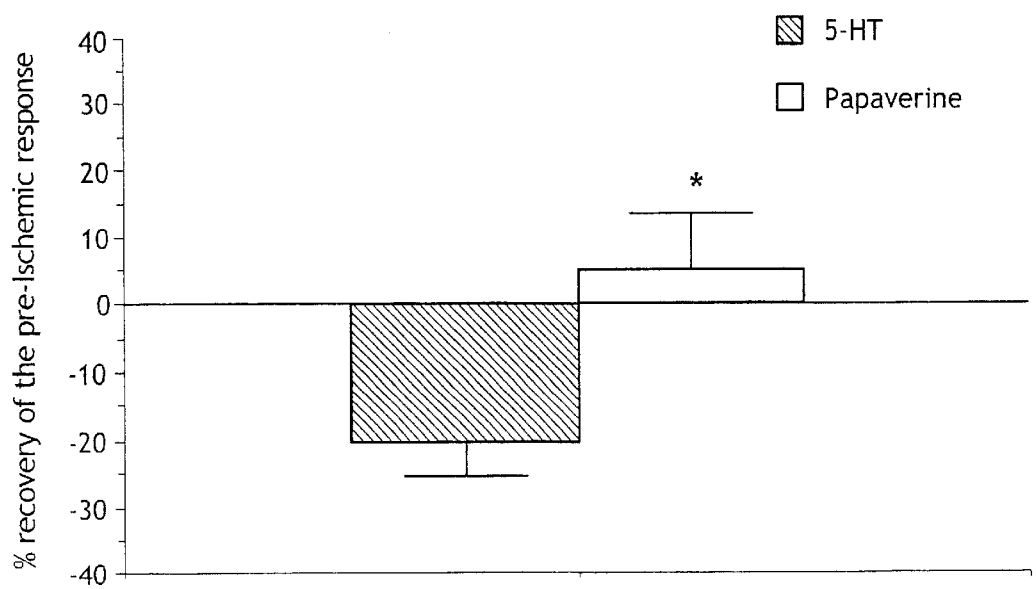

FIGS. 19A and 19B show, within the framework of protocol 3, the percentage of recovery of the pre-ischemic response to 5-HT and to papaverine after 8 hours of cold ischemia (1) after preservation without arginine (FIG. 19A), (2) with preservation with arginine (FIG. 19B) respectively.

The response to 5-HT is indicated by black squares, and that of papaverine by black squares.

Figure 20:
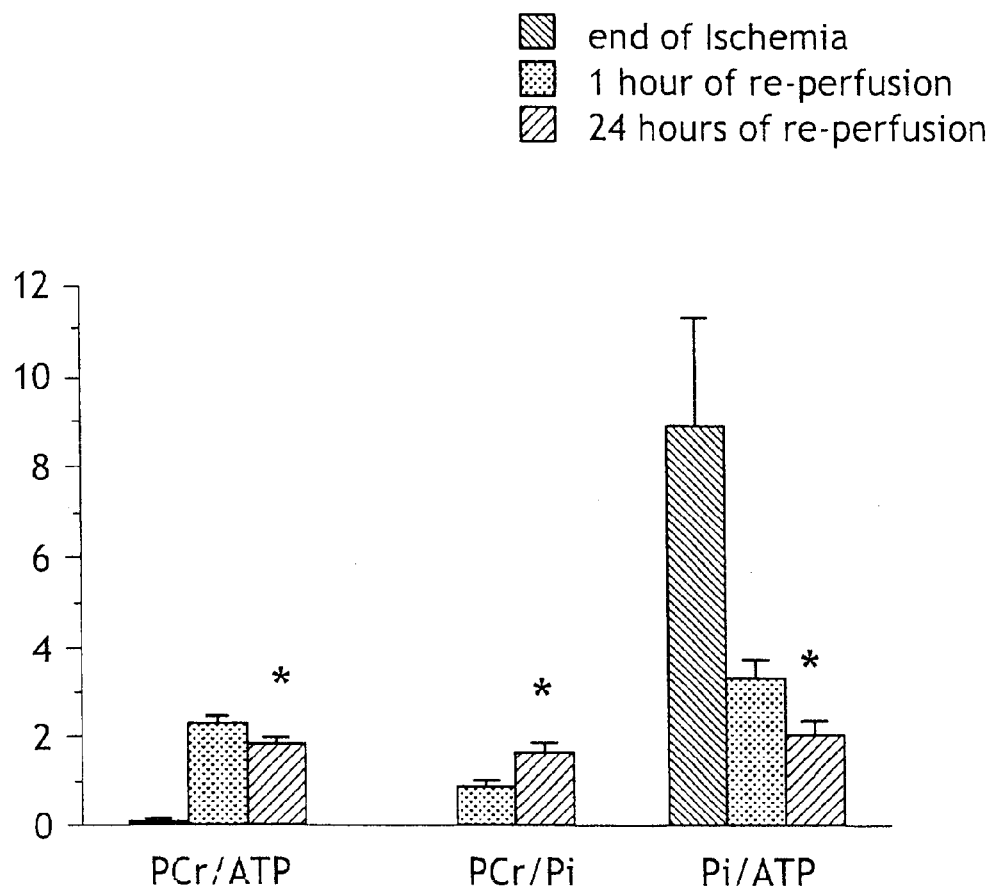

In FIG. 19B:
  *p<0.05 response to papaverine in comparison to the response to 5-HT FIG. 20 represents, within the framework of a protocol corresponding to 3 hours of ischemia with arrest and preservation in CRMBM solution, the ratios of different energy metabolites after 1 hour of re-perfusion (represented by the white histogram marked with black lines) and 24 hours of re-perfusion (represented by the histogram with white and black hatching).

The black histogram represents the end of ischemia.
  *p<0.05 24 hours of re-perfusion in comparison with 1 hour of re-perfusion The intracellular pool of PCr is totally depleted at the end of ischemia and is progressively restored during re-perfusion. FIG. 20 shows that the PCr/ATP and Pi/ATP ratios diminish significantly, whilst the PCr/Pi ratio significantly increases between 1 hour and 24 hours of re-perfusion.

The cardiac function significantly increases between 1 hour and 24 hours of re-perfusion, reaching 1331±81 mmHg/sec and 2081±333 mmHg/sec respectively.

Figure 21:
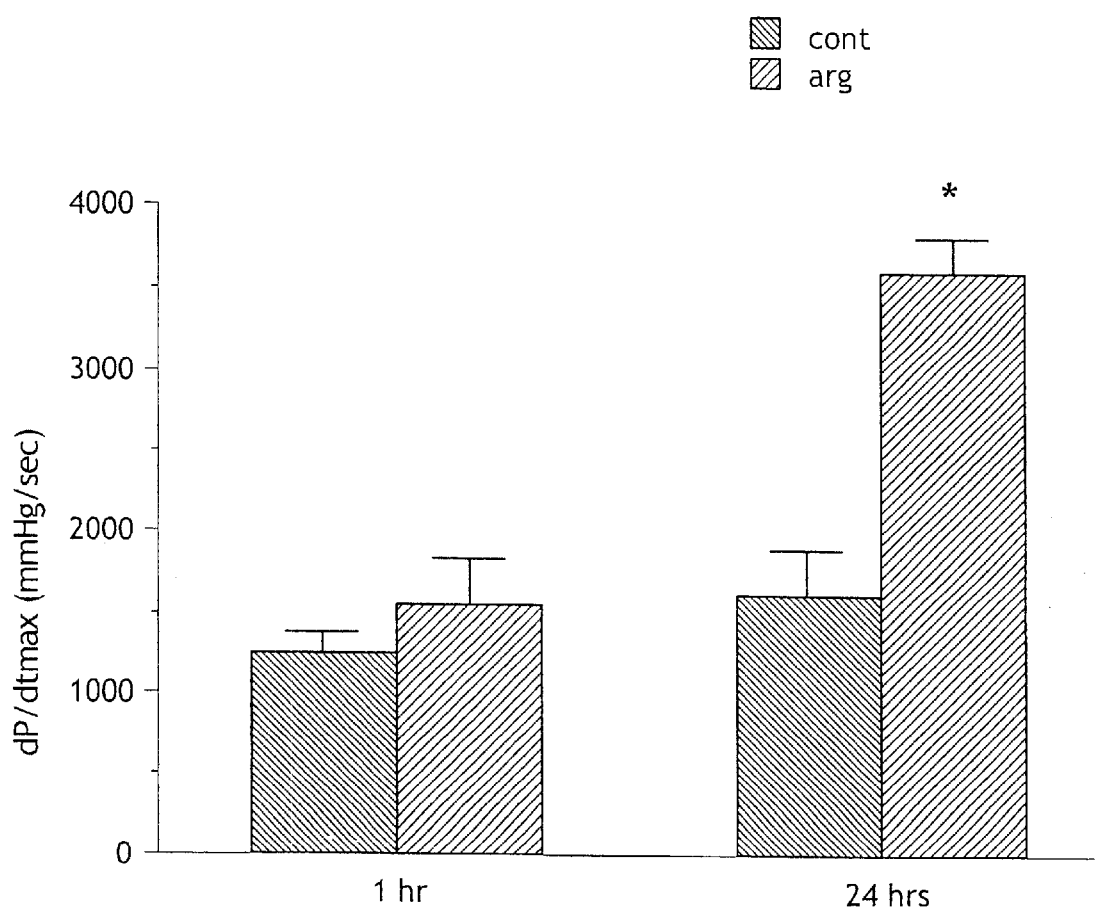

FIG. 21 shows, within the framework of the experimental protocol corresponding to 3 hours of ischemia with arrest and conservation in the CRMBM solution (not containing arginine) and in the invention solution (containing arginine), (1) the cardiac function with or without arginine after 1 hour of re-perfusion (see the left of the diagram), (2) the cardiac function with or without arginine after 24 hours of re-perfusion (see to the right of the diagram).

The cardiac function, as represented by the derivative of developed pressure ($dP/dt_{max}$), is indicated by the black histogram without arginine, and by the histogram with white and black hatching with arginine.

*p<0.05 with arginine in comparison to without arginine

EXAMPLES

Example 1

Model of an Isolated Perfused Heart 1.1. Preparation of the Perfused Heart

The hearts are removed from male Sprague Dawley rats of 350 to 375 g and anaesthetised by intraperitoneal injection of pentobarbital. The hearts are then perfused following the isovolumic contracting heart model. In this model, the heart is perfused with Krebs-Henseleit buffer at 37° C., without phosphate, in a retrograde manner via the aorta, at a constant pressure of 100 mmHg An incompressible balloon, placed in the left ventricle makes the contraction isovolumic. This model makes it possible to evaluate the cardiac function, by the developed pressure and to measure the compliance by measurement of the diastolic pressure.

1.2 Perfusion Apparatus

The perfusion device is composed of different reservoirs temperature controlled to 37° C. thanks to a continuous circulation of water. An independent circuit is provided for the reservoir containing the cardioplegic solution, maintained at 4 or 7.5° C. In the magnetic resonance spectroscopy (MRS) tube, the coronary discharges are evacuated by aspiration thanks to a rotating pump and are collected at given intervals to make different biochemical mixtures.

1.3. Perfusion Solutions

During periods of normoxic perfusion, the solution used is Krebs-Hensleit bicarbonate- buffer. The cardioplegic solution used to arrest and preserve the heart is variable.

1.4. MRS of P-31 Experiments

The MRS of P-31 spectrums are obtained at 81MHz by using a Bruker-Nicolet WP-200 spectrometer interfaced to a 4.7 Tesla vertical magnet, equipped with a selective probe 20 mm in diameter. The homogeneity of the magnetic field is carried out by using the proton signal in the sample contained in the approximate volume of the bobbin. The spectrums are acquired in 5 minutes by the summation of 428 free induction signals with an impulsion angle of 45° and a repetition time of 0.7 sec. The spectral width is from 6000 Hz and the memory size is 2K. Before the Fourier transformation, the free induction signal is multiplied by an exponential function generating a 20 Hz enlargement of the rays.

1.4.1 Analysis of the SRM of P-31 Data

The signals observed in the RMN spectrum of the P-31 are those of inorganic phosphate, phosphocreatine and the 3 phosphorous molecules of ATP. In certain spectrums a signal attributed to phosphomonesters (phosphate sugars) can be observed. The areas and the positions of resonance are determined by using the NMR1 program (New Methods Research Syracuse, N.Y.) on an IBM Risc System 6000 operating system.

1.4.2. Quantification of the Phosphorated Derivatves

The areas measured are corrected by taking into consideration the saturation factors determined by comparing the acquired spectrums to completely relaxed spectrums. The areas of different metabolites can thus be converted into concentrations by referring to the ATPβ area, taking into consideration a cytosolic concentration of 11.6 mM for the ATP (determined by high pressure liquid chromatography).

1.4.3. Measurement of Intracellular pH

The pH value is calculated from chemical displacement of the inorganic phosphate, in relation to the phosphocreatine resonance. In fact, its position in the spectrum is independent of pH, making it possible to link the chemical displacement of the signal to the pH thanks to a volumetric analysis curve.

1.5. Biochemical Analyses.

1.5.1. Measurement of the Heart Discharges.

Measurement of Creatine Kinase

The creatine kinase measured in the discharges is a good indicator of cellular integrity, the leakage of creatine kinase being proportional to the strength of the cellular lyse. The total CK activity is measured following the Rosalki method at 30° C. by using a sigma kit [Rosalki, S. B. An improved procedure for serum creatine phosphokinase determination. *J. Lab. Med.* 69,696–705 (1967).] A small volume of discharge is frozen in order to be able to later measure, the phosphate and the lactate as well as purines.

Phosphate Measurement

The phosphate is measured by colorimetry [Ames, B. N. Assay of inorganic phosphates, total phosphate and phosphatases. *Methods in Enzymology.* 8, 115–118 (1996)]

Lactate Measurement

The lactate is measured in an enzymatic manner [Gutman, I. and Wahlefeld. A.W.L-(+)- Lactase. Determination with lactate dehydrogenase and NAD. In "Methods of Enzymatic Analysis" (H. U. Bergmeymer), 3, 1464–1468. Acad Press NY, N.Y. 1974].

Purine Measurement

The measurement of purines is carried out by HPLC in an isocratic method [Wynants, J., et al. Optimization of a HPLC method for the determination of nucleotides and their catabolites. Application to cat and rabbit heart perfusates. *J Chromatogr.* 386, 297–275 (1951)] on B(45) select RP Lichrosorb column with the aid of a chromotographic device (LKB, Bromma, Sweden) comprising a pump (model 2150), a variable wavelength detector (model 2151), a regulator (model 2152) as well as an injection valve (Rheodyne 7125). The data is acquired by using an integration program KONTRON for PC (Kontron Instruments Munich FRG). The revealed purines are adenosine, inosine, allopurinol, xanthine and hypoxanthine.

1.5.2. Measurement in the Frozen Hearts

At the end of each experiment, the hearts are rapidly plunged into liquid nitrogen (freeze-clamping). The hearts are then placed in the freezer at −80° C. for later metabolic analyses and the determination of their water content.

Determination of the Water Content

The pieces of heart are defrosted, weighed, dehydrated for 48 hours then re-weighed after this loss of water. This technique makes it possible to evaluate the percentage of water in the tissues and to deduce the quantity of oedemea after re-perfusion.

Measurement of Creatine Kinase

During the measurements, about 30 mg of heart is defrosted and homogenised in a potassium phosphate buffer, the measurement of the creatine kinase is then carried out by the same enzymatic method as with the discharges. The enzymatic activities are expressed in international units (UI) per milligram of cardiac proteins measured following the Lowry and Coll method [Lowry, O. H., et al., R. J. Protein measurement with the Folin phenol reagent. *J. Biol. Chem* 193, 265–275 (1951)].

Measurement of Lactate Dehydrogenase (LDH)

The activity of the LDH is measured by the Bernstein and Everse method [Bernstein, L. K and Everse, J. Determination of the isoenzyme levels of lactate dehydrogenase. *Methods Enzymol.* 41, 47–52 (1975)] in the hearts treated with a potassium phosphate buffer.

Nucleotide Measurement by High Pressure Liquid Chromatography (HPLC).

The nucleotides are measured in the perchloric extracts of frozen hearts at the end of the experiment. The nucleotide measurement is carried out by HPLC in gradient mode on the RP-18 Lichrospher column on the same chromatographic device as the purine measurement. The total content in adenylic nucleotides (ATP+ADP+AMP=TAN) is shown in the results.

Measurement of the Amino Acids by High Pressure Liquid Chromatography (HPLC).

The free amino acids are measured in the perchloric extracts by using the Pico-Tag method (Waters) based on the results of Cohen et al [Cohen, S. A., et al., PITC derivatives in amino acid analysis. *Nature.* 320, 769–770 (1986)].

Example 2

Abdominal Heterotopic Cardiac Transplantation in the Lewis Rat

Male Lewis rats of 300 to 375 g are used as donors and recipients.

All the animals receive care and are kept in an environment conforming to the legislation regulating animal experimentation. Anaesthesia is induced and maintained with ether. The transplantation progresses following a clean, non sterile procedure.

Donor Preparation

After anaesthesia, a xyphopubian median laparotomy is performed and the aorta and the vena cava are controlled at the sub-renal level. 300UI of heparine are injected in the inferior vena cava, a long catheter is introduced into the aorta in a retrograde manner and cardiac arrest is induced by injection of 40 ml of cardioplegic liquid. The thorax is then reached by an anterior costal flap. 10 supplementary ml of cardioplegic liquid are injected through the sub-diaphragmatic inferior vena cava, in order to purge the cardiac cavities. The inferior vena cava, upper right and left are linked. The pulmonary artery is cut close to its branching and the aorta, at the foot of the BCAT. Finally the pulmonary veins are immediately immersed in the cardioplegic liquid at 4° C.

Preparation of the Recipient

After anaesthesia, a xyphopubian median laprotomy is performed. The aorta and the vena cava are controlled and exposed sub-renally. After electrocoagulation of the arteries and lumber veins, the vessels are clamped by a double clamp approximator.

The transplanted organ is placed transversely to the left of the aorta of the recipient, in the abdominal cavity, localised hypothermia is maintained with the aid of an ice cube. The aortic suture is carried out first (ternino-lateral anastomose between the aorta of the donor and the aorta of the recipient in polyamide monofil BV70 10/0-needle, then anastomose between the pulmonary artery of the donor and the vena cava of the recipient is carried out in the same way). Progressive de-clamping of the vessels downstream then upstream is carried out whilst the heart is reheated with the aid of serum at 37° C. After verification of hemastasis, the abdomen is then closed on 2 levels by an overcast stitch.

In the $24^{th}$ hour the animal is again anaesthetised for a $2^{nd}$ laparotomy. The functional appearance of the transplanted organ is noted. The transplanted organ is removed, then cannulated and perfused with Krebs for hemodynamic and metabolic study by phosphorous-31 magnetic resonance spectroscopy. The animal is then destroyed.

Comparative Example 3

Protocol 1: hemodynamic and metabolic evaluation by magnetic resonance spectroscopy of P-31 on hearts subjected to a total ischemia of 12 hours, after cardioplegic arrest on a preparation of isolated, perfused heart.

In this protocol, 4 cardioplegic solutions have been compared, the UW solution, the Broussais solution, the St Thomas solution and the CRMBM solution. The results show a better preservation of the metabolism and cellular integrity during ischemia and re-perfusion after an ischemia of 12 hours with the CRMBM solution, like that which has already been observed in a 6 hour protocol of ischemia (not shown). Functional recovery is very significantly improved with this solution after ischemia of 12 hours as it reaches 50% in this group although it is practically zero with the other solutions.

Protocol 2: Metabolic and hemodynamic evaluation on the model of heterotopic transplantation in abdominal position in the rat.

The heterotopic method of transplantation makes it possible to carry out physiological re-perfusion (with blood, progressive de-clamping, prolonged cardiac assistance). In addition, it makes it possible to evaluate long term metabolic and functional recovery.

The hearts are divided into 2 groups in this study:

Group A (control): The transplant is carried out immediately after removal (the duration of ischemia is about 40 mn).

Group B: the heart removed from the donor undergoes cold ischemia of 5 hours 20 minutes before transplantation (total ischemia of 6 hours counting the duration of carrying out the surgical procedure of the transplant).

After implantation of the heart, the animal recipient is closed up and the heart is examined after a period of 24 hours. A study of the heart is first of all carried out in situ on the whole animal by MRS of the P-31 on the Biospec device by using a $^1H$-$^{31}P$ bobbin with double connection contact 1.5 cm in diameter. Its morphological appearance is equally examined then, as the heart does not work in this model, the heart is excised and a hemodynamic evaluation is carried out on an isovolumic heart model with energy metabolism evaluation by magnetic resonance spectroscopy (study on the Bruker-Nicolet WP2000 spectrometer coupled to a vertical magnet of 4.7T). The biochemical measurements are equally carried out in the discharges and the frozen hearts at the end of the experiments.

The transplanted hearts in the 2 groups all resumed regular

The transplanted hearts in the 2 groups all resumed regular contractions at the time of de-clamping. After 24 hours the hearts examined in situ by MRS show similar levels of energy metabolites whatever the duration of the ischemia. In the same way the explanted and perfused hearts are characterised in the two groups by similar metabolic and functional indices.

The results obtained from the heterotopic transplant model in rats show that the perfected solution gives good protection in this model and validates the results acquired in the isolated, perfused heart model.

Protocol 3: improvement of the CRMBM solution by the addition of L-arginine: hemodynamic and metabolic study of the isolated and perfused heart model.

Introduction of L-arginine to the preservation solution has been studied in the previously described isolated, perfused heart model subjected to 8 hours of ischemia. The results show an improvement of functional post-ischemic recovery and a greater pool of amino acids during re-perfusion.

Protocol 4: comparison of the CRMBM solution with the recently patented Celsior solution: hemodynamic and metabolic study on the isolated and perfused heart model.

The study carried out on the isolated, perfused heart, subjected to 8 hours of ischemia demonstrates the obtaining of a better protection of membrane integrity with the CRMBM solution, as well as particularly attesting a reduced loss of creatine kinase during re-perfusion.

Example 3

Metabolic and Funtional Effects of Cardioplegic Solutions at Low Concentrations in Potassium for Long Term Preservation of the Heart In the aim of minimising the secondary effects linked to potassium, two concentrations in potassium (4 mM and 10 mM) have been evaluated in the preservation solution.

The composition of an invention solution containing 4 mM of potassium is like the one described above, and notably comprises KCl (2 mM) and $KH_2PO_4$ (2 mM).

The composition of a solution containing 10 mM of potassium is as described above, and notably comprises KCl (2 mM) and $KH_2PO_4$ (8 mM).

The magnetic resonance spectrometry of phosphorous-31 is used throughout the experimental protocol in order to follow the energy metabolism and the intracellular pH.

The functional recovery is measured before and after the ischemic period.

Biochemical measurements are equally carried out in the coronary discharges and in frozen hearts at the end of re-perfusion in order to determine the membrane damage.

The obtained results make it possible to show (cf FIGS. 15, 16A and 16B) that the reduction in the potassium concentration in the cardioplegic solution CRMBM improves the functional recovery and limits the membrane damage of rat hearts subjected to hypothermic ischemia of 8 hours and re-perfused whilst preserving the energy rich compounds.

Example 4

Effect of the Addition of L-arginine on the Variations of Amino Acid and Adenylic Nucleotide Concentrations During Long Term Ischemia and Re-perfusion of the Rat Heart: Effect of the Addition of L-arginine Different work carried out in these last years have shown that a sequence of ischemia and re-perfusion led to deterioration of the myocardiac content of amino acids in experimental animal models and in human hearts.

The influence of the presence of L-arginine in the cardioplegic invention has been evaluated on the intracellular concentrations of amino acids, of nucleotides and PCr at the end of ischemia and at the end of re-perfusion (cf FIGS. 17A, 17B, 18A and 18B).

The determination of the metabolites has been carried out by high performance liquid chromatography (HPLC).

The addition of L-arginine in the solution limits the depletion of the pool of amino acids during re-perfusion and improves post-ischemic functional recovery without however affecting the content in adenylic nucleotides.

Example 5

Effect of the Addition of L-arginine on the Function of the Endothelium and Smooth Vascular Muscle 5-hydroxytryptamine (5-HT) and papaverine have been used to analyse the variations of vasodilatory responses dependent and independent respectively on the endothelium during pre- and post-ischemic periods.

Before ischemia, the coronary flow is measured in each group during perfusion with the normal buffer solution and during the perfusion of 5-HT and papaverine. After ischemia, the recovery percentage of the pre-ischemic response of coronary flow to the perfusion of 5-HT and papaverine is calculated.

In the control group, the vasodilatory responses to the 5-HT and papaverine are completely lost and vasoconstriction is observed with the two drugs.

On the other hand, in the group receiving L-arginine, the vasodilatory response dependent eon the endothelium is lost whilst a slight recovery of the pre-ischemic response to papaverine is observed, indicating that the smooth vascular muscle is less affected than the coronary endothelium. (cf FIGS. 19A and 19B).

Example 6

Functional Recovery and Energy Metabolism During Short and Long Term Re-perfusion in the Heterotopic Transplant of Rat Heart Model A heterotopic transplant of rat heart model has been developed, working where the function and the metabolism can be simultaneously analysed. In this model the functional and metabolic recovery has thus been studied after 1 hour and 24 hours of re-perfusion after ischemia of 3 hours, protected by the invention solution.

The study has made it possible to analyse the long term recovery of the heart, comparing 1 hour and 24 hours of re-perfusion.

The study shows an improvement in functional recovery after 24 hours of re-perfusion, in comparison to 1 hour of re-perfusion, combined with an improvement of energy metabolism.

The analysis of the energy metabolite ratios (cf FIG. 20) suggests a regeneration of the intracellular pool of ATP after 24 hours of re-perfusion, in comparison to 1 hour of re-perfusion, able to be combined with the re-synthesis of ATP precursors. In fact, during the early stage of re-perfusion, there is a loss of metabolic precursors of ATP by the departure of these compounds into the extra-cellular environment. It is thus interesting to see if the cell will be capable of re-synthesising these precursors. In the conditions of ischemia and re-perfusion Of the present invention, recovery of energy metabolism is obtained (cf metabolite ratios), which suggests an actual re-synthesis of the metabolic precursors of ATP.

The effect of L-arginine has equally been studied in short term and long term re-perfusion (cf FIG. 21). The first results obtained on functional recovery of the heart show a beneficial effect of L-arginine as much after 1 hour of re-perfusion as after 24 hours of re-perfusion.

What is claimed is:

1. Solution for at least one of perfusion, preservation and re-perfusion during organ transplantation, comprising:

| | |
|---|---|
| $K^+$ | at a concentration of about 4 to about 7 mM, |
| $Ca^{2+}$ | at a concentration of about 0.2 to about 0.3 mM, |
| $Mg^{2+}$ | at a concentration of about 13 to about 16 mM, |
| glutamate | at a concentration of 18 to about 22 mM, |
| arginine | at a concentration of about 2 to about 4 mM, |
| adenosine | at a concentration of about 0.5 to about 1 mM. |

2. The solution according to claim 1, further comprising at least one water resistant agent selected from the group consisting of lactobionic acid, mannitol and raffinose.

3. The solution according to claim 1, further comprising at least one agent to trap free radicals selected from the group consisting of glutathion (reduced form), allopurinol, and mannitol.

4. The solution according to claim 1, comprising:

| | |
|---|---|
| $K^+$ | at a concentration of about 4 to about 7 mM, |
| $Ca^{2+}$ | at a concentration of about 0.2 to about 0.3 mM, |
| $Mg^{2+}$ | at a concentration of about 13 to about 16 mM, |
| glutamate | at a concentration of 18 to about 22 mM, |
| arginine | at a concentration of about 2 to about 4 mM, |
| adenosine | at a concentration of about 0.5 to about 1 mM. | at least one water resistant agent,
at least one agent trapping free radicals
Osmolarity 340 mM
pH 7.4.

5. Solution for at least one of perfusion, preservation and re-perfusion during organ transplantation, comprising:

| | |
|---|---|
| $K^+$ | of about 4 to about 7 mM, |
| $Ca^{2+}$ | of about 0.2 to about 0.3 mM, |
| $Na^+$ | of about 108 to about 132 mM, |
| $Mg^{2+}$ | of about 13 to about 16 mM, |
| glutamate | of about 18 to about 22 mM, |
| arginine | of about 2 to about 4 mM, |
| adenosine | of about 0.5 to about 1 mM, |
| mannitol | of about 27 to about 33 mM, |
| allopurinol | of about 0.9 to about 1.1 mM, |
| glutathion (reduced form) | of about 2.7 to about 3.3 mM, |
| raffinose | of about 25 to about 35 mM, |
| lactobionic acid | of about 80 to about 120 mM, |
| pH | of about 7.2 to about 7.4, |
| osmolarity | of about 330 to about 360 mOsm. |

6. The solution according to claim 5, in which $Na^+$ is in the form NaOH, $K^+$ is in the form KCl and $KH_2PO_4$, at a concentration of about 2 to about 3.5 mM KCl and about 2 to about 3.5 mM $KH_2PO_4$, $Ca^{2+}$ is in the form of $CaCl_2, 2H_2O$ and $Mg^{2+}$ is in the form $MgCl_2.6H_2O$.

7. A method for the preservation of organs, comprising contacting an organ with the solution of claim 1, for a duration of at least 12 to 15 hours.

8. A method of maintaining the cellular and metabolic integrity of an organ after ischemia, said integrity being detectable by measurement of the activities of at least one of lactate dehydrogenase and creatine kinase and/or by measurement of at least one of the following metabolites: purines, adenylic nucleotides, inosine monophosphate, adenosine triphosphate, amino acids, inorganic phosphate, lactate, and phosphocreatine; comprising contacting an organ with the solution of claim 1 or a duration of at least 12 to 15 hours.

9. A method of ensuring post ischemic functional recovery of an organ, this functional recovery being measureable by the measurement of at least one of the following hemodynamic parameters: coronary flow, developed pressure, cardiac frequency, and diastolic pressure, comprising contacting an organ with the solution of claim 1 for a duration of at least 12 to 15 hours.

10. A method for the preservation of organs, comprising contacting an organ with the solution of claim 5 for a duration of at least 12 to 15 hours.

11. A method of maintaining the cellular and metabolic integrity of an organ after ischemia, said integrity being detectable by measurement of the activities of at least one of lactate dehyudrogenase and creatine kinase and/or by measurement of at least one of the following metabolites: purines, adenylic nucleotides, inosine monophosphate, adenosine triphosphate, amino acids, inorganic phosphate, lactate, and phosphocreatine; comprising contacting an organ with the solution of claim 5 for a duration of at least 12 to 15 hours.

12. A method of ensuring post ischemic functional recovery of an organ, this functional recovery being measureable by the measurement of at least one of the following hemodynamic parameters: coronary flow, developed pressure, cardiac frequency, and diastolic pressure, comprising contacting an organ with the solution of claim 5 for a duration of at least 12 to 15 hours.

* * * * *